US 7,460,940 B2

(12) United States Patent
Larsson et al.

(10) Patent No.: US 7,460,940 B2
(45) Date of Patent: Dec. 2, 2008

(54) METHOD AND ARRANGEMENT FOR INTERPRETING A SUBJECTS HEAD AND EYE ACTIVITY

(75) Inventors: Petter Larsson, Hjalteby (SE); Trent Victor, Göteborg (SE)

(73) Assignee: Volvo Technology Corporation, Gothenburg (SE)

( * ) Notice: Subject to any disclaimer, the term of this patent is extended or adjusted under 35 U.S.C. 154(b) by 869 days.

(21) Appl. No.: 10/605,637

(22) Filed: Oct. 15, 2003

(65) Prior Publication Data

US 2005/0073136 A1 Apr. 7, 2005

Related U.S. Application Data

(60) Provisional application No. 60/418,171, filed on Oct. 15, 2002.

(51) Int. Cl.
*B60R 22/00* (2006.01)
(52) U.S. Cl. .............................. 701/49; 701/45; 701/36; 280/735; 180/272
(58) Field of Classification Search .................. 351/206, 351/209; 340/576; 706/20; 701/1, 49, 45, 701/36; 280/735; 180/272
See application file for complete search history.

(56) References Cited

U.S. PATENT DOCUMENTS

| 4,439,755 | A | * | 3/1984 | LaRussa ..................... 340/980 |
| 5,360,971 | A | * | 11/1994 | Kaufman et al. ............ 250/221 |
| 5,371,510 | A | | 12/1994 | Miyauchi et al. ............... 345/7 |
| 5,517,021 | A | * | 5/1996 | Kaufman et al. ............ 250/221 |
| 5,570,698 | A | | 11/1996 | Liang et al. |
| 5,585,785 | A | | 12/1996 | Gwin et al. |

(Continued)

FOREIGN PATENT DOCUMENTS

EP 0548829 A1 6/1993

(Continued)

OTHER PUBLICATIONS

Study on eye gaze estimation; Jian-Gang Wang; Sung, E.; Systems, Man, and Cybernetics, Part B, IEEE Transactions on vol. 32, Issue 3, Jun. 2002 pp. 332-350; Digital Object Identifier 10.1109/TSMCB.2002.999809.*

(Continued)

*Primary Examiner*—Cuong H Nguyen
(74) *Attorney, Agent, or Firm*—Novak Druce + Quigg LLP

(57) ABSTRACT

Method for analyzing ocular and/or head orientation characteristics of a subject. A detection and quantification of the position of a driver's head and/or eye movements are made relative to the environment. Tests of the data are made, and from the data, locations of experienced areas/objects-of-subject-interest are deduced. When a driver of a vehicle is the subject, these areas/objects-of-driver-interest may be inside or outside the vehicle, and may be constituted by (1) "things" such as audio controls, speedometers and other gauges, and (2) areas or positions such as "road ahead" and lane-change clearance space in adjacent lanes. In order to "standardize" the tracking data with respect to the vehicle of interest, the quantification of the position of the driver's head is normalized to the reference-base position thereby enabling deducement of location(s) where the driver has shown an interest based on sensed information regarding either, or both of (1) driver ocular orientation or (2) driver head orientation.

22 Claims, 16 Drawing Sheets

U.S. PATENT DOCUMENTS

| | | | |
|---|---|---|---|
| 5,689,241 A * | 11/1997 | Clarke et al. | 340/575 |
| 5,764,139 A | 6/1998 | Nojima et al. | 340/461 |
| 5,786,765 A | 7/1998 | Kumakura et al. | |
| 5,900,819 A | 5/1999 | Kyrtsos | |
| 5,949,345 A | 9/1999 | Beckert et al. | 340/815.41 |
| 5,982,352 A * | 11/1999 | Pryor | 345/156 |
| 6,008,800 A * | 12/1999 | Pryor | 345/173 |
| 6,091,334 A | 7/2000 | Galiana et al. | 340/576 |
| 6,120,461 A | 9/2000 | Smyth | |
| 6,130,617 A | 10/2000 | Yeo | |
| 6,134,492 A * | 10/2000 | Breed et al. | 701/49 |
| 6,154,559 A | 11/2000 | Beardsley | 382/103 |
| 6,188,315 B1 | 2/2001 | Herbert et al. | 340/438 |
| 6,228,038 B1 * | 5/2001 | Claessens | 600/558 |
| 6,331,152 B1 * | 12/2001 | Holle | 482/4 |
| 6,397,137 B1 * | 5/2002 | Alpert et al. | 701/49 |
| 6,437,759 B1 * | 8/2002 | Turner et al. | 345/8 |
| 6,496,117 B2 | 12/2002 | Gutta et al. | 340/576 |
| 6,720,949 B1 * | 4/2004 | Pryor et al. | 345/158 |
| 6,879,969 B2 * | 4/2005 | Engstrom et al. | 706/20 |
| 7,027,621 B1 * | 4/2006 | Prokoski | 382/118 |
| 7,042,440 B2 * | 5/2006 | Pryor et al. | 345/158 |
| 7,068,444 B2 * | 6/2006 | Nishi | 359/708 |
| 7,098,891 B1 * | 8/2006 | Pryor | 345/158 |
| 7,224,382 B2 * | 5/2007 | Baker | 348/46 |
| 7,245,273 B2 * | 7/2007 | Eberl et al. | 345/7 |
| 7,363,233 B1 * | 4/2008 | Levine | 705/1 |
| 7,375,728 B2 * | 5/2008 | Donath et al. | 345/427 |
| 2001/0028309 A1 | 10/2001 | Torch | 340/575 |
| 2002/0101568 A1 * | 8/2002 | Eberl et al. | 351/211 |
| 2002/0120374 A1 | 8/2002 | Douros et al. | 701/29 |
| 2003/0076280 A1 * | 4/2003 | Turner et al. | 345/7 |
| 2003/0128182 A1 * | 7/2003 | Donath et al. | 345/156 |
| 2004/0027451 A1 * | 2/2004 | Baker | 348/46 |
| 2004/0066376 A1 * | 4/2004 | Donath et al. | 345/169 |
| 2005/0073136 A1 * | 4/2005 | Larsson et al. | 280/735 |
| 2006/0072215 A1 * | 4/2006 | Nishi | 359/708 |

FOREIGN PATENT DOCUMENTS

| | | |
|---|---|---|
| EP | 0548829 B1 | 6/1993 |
| EP | 0901000 A2 | 3/1999 |
| JP | 06-143107 | 5/1994 |
| JP | 10-243464 | 9/1998 |
| JP | 10-262107 | 9/1998 |
| JP | 11-085458 | 3/1999 |
| JP | 11-102198 | 4/1999 |
| WO | WO 9849028 A1 | 11/1998 |

OTHER PUBLICATIONS

A Drowsiness and Point of Attention Monitoring System for Driver Vigilance; Batista, J.; Intelligent Transportation Systems Conference, 2007. ITSC 2007. IEEE, Sep. 30, 2007-Oct. 3, 2007 pp. 702-708; Digital Object Identifier 10.1109/ITSC.2007.4357702.*

Multimodal Face Detection, Head Orientation and Eye Gaze Tracking; Wallholf, F.; Ablabmeier, M.; Rigoll, G.; Multisensor Fusion and Integration for Intelligent Systems, 2006 IEEE International Conference on, Sep. 2006 pp. 13-18; Digital Object Identifier 10.1109/MFI.2006.265612.*

Photorealistic Attention-Based Gaze Animation; Itti, L.; Dhavale, N.; Pighin, F.; Multimedia and Expo, 2006 IEEE International Conference on, Jul. 2006 pp. 521-524; Digital Object Identifier 10.1109/ICME.2006.262440.*

Towards low-cost systems for measuring visual cues of driver fatigue and inattention in automotive applications; Bretzner, L.; Krantz, M.; Vehicular Electronics and Safety, 2005. IEEE International Conference on, Oct. 14-16, 2005 pp. 161-164 Digital Object Identifier 10.1109/ICVES.2005.1563634.*

Towards low-cost systems for measuring visual cues of driver fatigue and inattention in automotive applications; Bretzner, L.; Krantz, M.; Vehicular Electronics and Safety, 2005. IEEE International Conference on Oct. 14-16, 2005 pp. 161-164 Digital Object Identifier 10.1109/ICVES.2005.1563634.*

A miniature biomimetic gaze control system; Viollet, S.; Franceschini, N.; Robotics and Automation, 2004. Proceedings. ICRA '04. 2004 IEEE International Conference on, vol. 1, 2004 pp. 504-510 vol. 1; Digital Object Identifier 10.1109/ROBOT.2004.1307199.*

Modeling, tracking and interactive animation of faces and heads// using input from video; Essa, I.; Basu, S.; Darrell, T.; Pentland, A.; Computer Animation '96. Proceedings Jun. 3-4, 1996 pp. 68-79; Digital Object Identifier 10.1109/CA.1996.540489.*

Head-centered orientation strategies in animate vision; Grosso, E.; Ballard, D.H.; Computer Vision, 1993. Proceedings., Fourth International Conference on; May 11-14, 1993 pp. 395-402; Digital Object Identifier 10.1109/ICCV.1993.378188.*

Modeling, tracking and interactive animation of faces and heads// using input from video; Essa, I.; Basu, S.; Darrell, T.; Pentland, A.; Computer Animation '96. Proceedings, Jun. 3-4, 1996 pp. 68-79; Digital Object Identifier 10.1109/CA.1996.540489.*

Transition between virtual environment and workstation environment with projective head mounted display; Kijima, R.; Ojika, T.; Virtual Reality Annual International Symposium, 1997., IEEE 1997; Mar. 1-5, 1997 pp. 130-137; Digital Object Identifier 10.1109/VRAIS.1997.583062.*

A testbed for precise registration, natural occlusion and interaction in an augmented environment using a head-mounted projective display (HMPD); Hong Hua, Chunyu Gao; Brown, L.D.; Ahuja, N.; Rolland, J.P.; Virtual Reality, 2002. Proceedings. IEEE Mar. 24-28, 2002 pp. 81-89; Digital Object Identifier 10.1109/VR.2002.996508.*

Yuji Uchiyama, Shin-ichi Kojima, Takero Hongo, Ryuta Terashima, and Toshihiro Wakita, *Voice Information System Adapted To Driver's Mental Workload*, 2002, pp. 1871-1875, Proceedings of the Human Factors And Ergonomics Society 46th Annual Meeting 2002, Toyota Central Research & Development Labs, Inc., Nagakute, Aichi, Japan.

M. Sodhi, B. Reimer, J. L. Cohen (University of Rhode Islande, Kingston); E. Vastenburg, R. Kaars (Hogeschool Van Amsterdam, Holland); and S. Kirschenbaum (Naval Undersea Warfare Lab, Newport), *On-Road Driver Eye Movement Tracking Using Head-Mounted Devices*, pp. 1-7.

M. Hoedemaeker, S.N. de Ridder, W. H. Janssen, *Review of European Human Factors Research on Adaptive Interface Technologies for Automobiles*, May 14, 2002, pp. 1-60, TNO Human Factors, TNO Report, TM-02-C031, Netherlands Organisation for Applied Scientific Research, Soesterberg, Netherlands.

Chip Wood, Robert Leivian, Noel Massey, Jack Bieker, and John Summers, *Driver Advocate Tool™*, Mar. 18, 2002, pp. 1-5, Human Interface Lab-Pheonix, Motorola Labs, Motorola, Tempe, Arizona.

Delphi Automotive Systems, *Integrated Safety Systems—Delphi Technology Paper* 01/13.

Willie D. Jones, *Building Safer Cars*, IEEE Spectrum—Critical Challenges 2002, Jan. 2002, pp. 81-85.

Adcock, Ian, *Drivers on the Blink*, European Automotive Design, Feb. 2001, pp. 26-26.

Don Remboski, Judy Gardner, David Wheatley, Joshua Hurwitz, Tom MacTavish, and Robert "Mike" Gardner, *Driver Performance Improvement Through The Driver Advocate: A Research Initiative Toward Automotive Safety*, © 2000, pp. 1-10, 2000-01-CO75, Society of Automotive Engineers, Inc.

* cited by examiner

METHOD AND ARRANGEMENT FOR INTERPRETING A SUBJECTS HEAD AND EYE ACTIVITY

CROSS REFERENCE TO RELATED APPLICATIONS

The present application claims the benefit of provisional patent application No. 60/418,171, filed 15 Oct. 2002 and entitled METHOD AND ARRANGEMENT FOR INTERPRETING DRIVER ACTIVITY, the disclosure of which is expressly incorporated herein by reference in its entirety.

BACKGROUND OF INVENTION

1. Technical Field

The present invention relates to methods for the automated treatment of data; and more specifically, the invention relates to automated methods for analyzing and utilizing head and eye tracking data to deduce characteristics about the observed subject such as cognitive and visual distraction, as well as quantify work load levels.

2. Background Art

There is significant ongoing research related to driver fatigue, distraction, workload and other driver-state related factors creating potentially dangerous driving situations. This is not surprising considering that approximately ninety-five percent of all traffic incidents are due to driver error, of which, driver inattention is the most common causative factor. Numerous studies have established the relationship between eye movements and higher cognitive processes. These studies generally argue that eye movements reflect, to some degree, the cognitive state of the driver. In several studies, eye movements are used as a direct measure of a driver's cognitive attention level, and alternatively mental workload.

Knowing where a driver is looking is generally accepted as an important input factor for systems designed to avoid vehicular incidents, an in particularly, crashes. By ascertaining where a driver is looking, Human Machine Interaction (HMI) systems can be optimized, and active safety functions, such as forward collision warnings (FWC), can be adapted on the basis of driver-eye orientation and movements. This may be done as an offline analysis of many subjects, or using an online, or real-time algorithm to perhaps adapt such things as FCW thresholds to the current driver state.

As mentioned above, an interesting use for eye movements is in the ergonomics and HMI fields. For instance, such utilization may be made in determining best placements for Road and Traffic Information (RTI) displays, as well as analyzing whether a certain HMI poses less visual demand than another. These types of analysis can, and are made by studying subjects" eye movements while using the device —HMI. A primary drawback associated with current methods, however, is that there are few, if any, suitable automated tools for performing the analysis; in their absence, resort is commonly made to labor intensive, manual analysis.

A significant problem in current eye movement research is that every research team seems to use their own definitions and software to decode the eye movement signals. This makes research results very difficult to compare between one another. It is desirable to have a standard that defines visual measures and conceptions. ISO 15007 and SAEJ-2396 constitute examples of such standards in that they prescribe in-vehicle visual demand measurement methods and provide quantification rules for such ocular characteristics as glance frequency, glance time, time off road-scene-ahead and glance duration, and the procedures to obtain them. However, the two standards are based on a recorded-video technique, and rely on frame-by-frame human-rater analysis that is both time consuming and significantly unreliable. As the number of various in-vehicle information and driver assistance systems and devices increases, so will the probable interest for driver eye movements and other cognitive indicators. Thus, the need for a standardized, automated and robust analysis method for eye movements exists, and will become even more important in the future.

Certain eye tracking methods and analysis procedures have been statistically verified to the prescriptions of ISO 15007 and SAEJ-2396. These physical portions of the systems can be configured to be neither intrusive nor very environmentally dependent. At least one example is based on two cameras (a stereo head) being positioned in front of the driver. Software is used to compute gaze vectors and other interesting measures on a real-time basis, indicating such things as head position and rotation (orientation), blinking, blink frequency, and degree of eye-openness. Among other important features in this software are the real-time simultaneous computation of head position/rotation (orientation) and gaze rotation; a feature that has never before been available. Also, it is not sensitive to noisy environments such as occur inside a vehicle. Among other things, "noise" in the data has been found to be a significant factor impacting data-quality-degradation due to such things as variable lighting conditions and head/gaze motion.

It may seem that the previous work done in the area of eye tracking related research is reasonably exhaustive. Yet, as progress is made enabling eye tracking to be more robust and portable, this technology area continues to expand. There are, however, not many on-road studies of driving task-related driver characteristics, and to date, there has been no utilization of eye-tracking data on a real-time basis to calculate measures such as visual or cognitive distraction (see FIGS. 16-18). This is at least partially the result of the time consuming nature of manual segmentation and/or technical difficulties related to the non-portability of commonly used eye-tracking systems. However, in studies conducted in laboratory environments, a variety of algorithms have been developed. Many different approaches have been taken using, for example, Neural Networks, adaptive digital filters, Hidden Markov Models, Least Mean Square methods, dispersion or velocity based methods and other higher derivative methods. Many of these methods, however, are based on the typical characteristics of the eye tracker, such as sampling frequency, and do not work well with other such systems.

Heretofore, there has been no standard for defining what driver characteristic(s) are to be measured, and how they are to be measured. There is no standard that refers to the basic ocular segmentations including saccades, fixations, and eye closures. The standard only concerns glances; that is, the incidence of rapid eye movement across the field of vision.

Interestingly, no current methods take into account smooth eye movements or pursuits; that is, purposeful looks away from the driving path such as looking (reading) a road sign as it is passed. In fact, many studies are designed so that smooth pursuits will never occur, such as by assuring that there are no objects to pursue. This avoidance by current research is understandable; it can be difficult to differentiate a smooth pursuit from a saccade or a fixation. These characteristics are rarely mentioned in the literature. Regardless of the reason(s) that these characteristics have not been considered, smooth pursuits are taken into account with regard to the presently disclosed invention(s) because such smooth eye movement does occur quite often under real driving conditions.

Fundamental to driving a vehicle is the necessity to aim the vehicle, to detect its path or heading, and to detect potential collision threats whether they are from objects or events. This road scene awareness is a prerequisite to longitudinal and lateral control of the vehicle. It should be appreciated that road-center is not always straight ahead of the longitudinal axis of the vehicle, but is often off-centerline due to curves that almost always exist in road-ways to greater and lesser degrees. Even so, research shows that drivers tend to look substantially straight ahead (considering reasonable deviations for road-curvature), with their eyes on the road most of the time; that is, about eight-five to ninety-five percent of the time. Still further, prudence tells the average driver that glances away from the road center or travel path are best timed not to interfere with aiming the vehicle, and to coincide with a low probability of an occurrence of unexpected event or object encounter. Even so, the statistics above demonstrate that even prudent drivers are not always attentive to driving demands, nor are they consistently good managers of their own work loads and distractions when driving.

Driving is not a particularly demanding task in most instances. For example, it is estimated that during most interstate driving, less than fifty percent of a driver's perceptual capacity is used. Because of this, drivers often perform secondary tasks such as dialing cellular phones and changing radio channels. When secondary tasks are performed, a time-sharing glance behavior is exhibited in which the eyes are shifted back and forth between the road and the task. This temporal sharing of vision is an implication of having a single visual resource. One could say that the road is sampled while performing secondary tasks instead of the opposite. The problem, which induces collisions, is that unexpected things might happen during the interval when the eyes are off the road and reactions to these unexpected events or objects can be seriously slowed.

The new measures and analysis techniques presented herein exploit this fundamental and necessary driving eye-movement behavior of looking straight ahead or on the vehicle path trajectory. The measures give an accurate off-line assessment of the visual impact of performing visually, cognitively, or manually demanding in-vehicle tasks that have been found to be highly correlated with conventional measures. They also enable a comparison with normal driving. The measures presented herein are importantly also suitable for on-line calculation and assessment of this visual impact and thus represent real-time measures that can be used for distraction and work-load detection.

SUMMARY OF INVENTION

At least one characteristic of the present intention(s) is the provision of validated analysis methods and algorithms that facilitate: automated analysis of eye-movement data produced by head and/or eye-tracking systems, substantial elimination of human rating, and outputting filtered and validated characteristic data that is robust against errors and noise. Preferably, these facilitations are conducted in accordance with ISO/SAE and similarly accepted present and future standards.

Another aim is to adapt certain algorithms to a real-time environment. Another is to identify and provide driver supports that are based on visual behavior and that can assist the driver avoid potentially detrimental situations because of implemented systems that refocus the driver.

In one aspect, the present invention addresses the need for having one standard reference in a vehicle from which various objects and areas that might be of interest to a driver can be located relatively located. A standard frame of reference (defined by relative position/location/orientation {in the context of the present disclosure, utilization of the forward slash-mark, /, is utilized to indicate an "and/or" relationship} within the vehicle's interior) to which head/facial/eye tracking data taken from operators of varying size, stature and behavior can be translated is desirable in that it "standardizes" such data for elegant processing for the several purposes described herein.

In at least one embodiment, the presently disclosed invention may be defined as a method for analyzing ocular and/or head orientation characteristics of a driver of a vehicle. It should be appreciated that the analysis techniques or processes described are contemplated as being capable of being applied to stored tracking data that has typically been marked with respect to time, or real-time data, which by its nature, considers time as a defining factor in a data stream; hence the descriptive name, "real-time" data. In any event, this embodiment of the invention contemplates a detection and quantification of the position of a driver's head relative to the space within a passenger compartment of a vehicle. A reference-base position of a "bench-mark" driver's head (or portion thereof) is provided which enables a cross-referencing of locations of areas/objects-of-driver-interest relative thereto. It should be appreciated that these areas/objects-of-driver-interest may be inside or outside the vehicle, and may be constituted by (1) "things" such as audio controls, speedometers and other gauges, and (2) areas or positions such as "road ahead" and lane-change clearance space in adjacent lanes. In order to "standardize" the tracking data with respect to the vehicle of interest, the quantification of the position of the driver's head is normalized to the reference-base position thereby enabling deducement of location(s) where the driver has shown an interest based on sensed information regarding either, or both of (1) driver ocular orientation or (2) driver head orientation.

In the event that tracking information is available on both driver head and eye characteristics, sensed information regarding driver ocular orientation is preferentially utilized as basis for the deducement of location(s) of driver interest. A switch is made to sensed information regarding driver head orientation as basis for deducing where driver interest has been shown when the quality of the sensed information regarding driver ocular orientation degrades beyond a prescribed threshold gaze confidence level. As an example, this switch may be necessitated when the driver's eyes are occluded; that is, obscured or covered in some way that prevents their being tracked. The condition of being occluded is also contemplated to include situations in which the tracking sensor(s) is unable to track the eyes because, for example, of an inability to identify/locate relative facial features. For example, eyes-to-nose-to-mouth orientation and reference cannot be deduced (some tracking systems require that a frame of reference for the face be established in order to locate the eyes which are to be tracked and characterized by data values. When the face is not properly referenced, it is possible for some sensor systems to track, for instance, the subject's nostrils, which have been confused for the eyes, or eye-glasses that are being worn distort (refractionally) or obscure (sunglasses) the eye-image. Another example of the eyes being occluded is when the driver's head position departs away from an eyes-forward (predominant driving) orientation beyond an allowed degree of deviation. In these events, the eye(s) of the driver are effectively visually blocked from the tracking equipment (sensors) that is generating the eye-orientation data.

Preferably, a mathematic transformation is utilized to accomplish the normalization of the quantification of the position of the driver's head to the reference-base position. In an on-board installation, it is preferred that the mathematic transformation be performed using a vehicle-based computer on a substantially real time basis.

In one development (version) of the invention, probable positions of areas/objects-of-driver-interest relative to the reference-base position are prescribing. In this regard, such prescriptions act as templates against, or onto which the sensed data can be read or overlaid.

Alternatively, probable positions of areas/objects-of-driver-interest are defined relative to the reference-base position based on sensed driver ocular characteristics. In one exemplary development, such definitions of probable positions of areas/objects-of-driver-interest relative to the reference-base position can be established based on the sensed driver ocular characteristic of gaze frequency. Here, establishment of the gaze frequency is based on quantification of collected gaze density characteristics.

In one embodiment of the invention, an area/object-of-driver-interest (which is intended to be interpreted as also encompassing a plurality of areas/objects-of-driver-interest) is identified based on driver ocular characteristics (exemplarily represented as tracking data) by mapping the sensed driver ocular characteristics to the prescribed or defined probable locations of areas/objects-of-driver-interest relative to the reference-base position. That is, identification of an object or area that has been deduced as probably being of interest to a driver can be made by comparison of the observed data (head and/or eye tracking data) to a prescribed template as defined hereinabove, or by comparison to a known data set that has been correlated to particular objects and/or areas in which a driver would be potentially interested.

An exemplary example would be that an area-based template is devised for a particular vehicle, and relative frequencies at which a driver looks at various locations/object is identified. For instance, it may be found that a typical driver looks in a substantially straight-forward direction about forty percent of driving time and the gauge cluster, including the speedometer about twenty percent of driving time. It is also known that spatially, the center of these two areas is one below the other. Therefore, utilizing gaze direction data (regardless of whether it is based on head orientation or eye (ocular) orientation), the relative location of the road center and the instrument cluster can be deduced for a particular driver. Once that basic frame of reference is established, correspondence to reality for the particular vehicle can be deduced, and a translation to a reference frame can be determined. Still further, glances to the vehicle's audio controls can also be deduced, for instance, if statistically, it is known that a typical driver looks to the audio controls approximately ten percent of normal driving time. Once a period of "learning time" has been recorded, the relative locations of many areas/objects-of-driver-interest can be ascertained on a statistical basis; even independent of any known map of objects/areas, or reference frame in the vehicle.

In another aspect, the invention entails tailoring prescribed functionalities performed by the vehicle based on the mapped driver ocular characteristics. This may be as simple as adapting a distraction warning to sound when it is detected that the driver has looked away from the road too long, to causing an increase of the buffer zone maintained behind a leading vehicle by an adaptive cruise control system.

In one particularly advantageous embodiment, it has been discovered that these areas/objects-of-driver-interest can be identified based either in part, or exclusively on sensed information regarding driver ocular orientation exclusively constituted by a measure of gaze angularity. With respect to at least a reference frame within a particular vehicle (exemplarily identified as a particular make and model of an automobile), angular location of an area/object is particularly elegant because the need to consider distances are removed. That is to say, if an area-location were to be identified as statistically (probabilistically) representing an area/object of probable driver interest, the distance at which that area is located away from the reference frame must be known. This turns on the fact that an a defined area expands from a focal point much like a cone does from its apex. An angle from the apex, however, is a discrete measure (see FIG. 11).

In an exemplary version of the invention, the measure of gaze angularity is derived from a sensed eyeball-orientation-based gaze-direction vector. This could be taken from the observation of one eyeball, but preferably, it is taken as a conglomeration of observations taken from both eyeballs. Therefore, the representative vector is more accurately described as a vector emanating from the region of the subjects nose bridge, and oriented parallel to an average of observed angularity.

While the invention has been described with respect to particulars in terms of eyeball angularity herein above, it is also contemplated that related, if not similar results can be obtained from making similar observations based on head orientation. In general, the comparison can be described as using the direction in which the nose points (head-based), as opposed to the direction in which the eyes are oriented from the reference frame defined by the orientation of the reference frame, defining probable positions of areas/objects-of-driver-interest relative to the reference-base position based on sensed head orientation.

In at least one embodiment, the definitions of probable positions of areas/objects-of-driver-interest is determined relative to the reference-base position based on sensed head orientation from which a face-forward direction is deduced. In this case, as with eyeball trajectory measurement data, particular head orientations, and hence a face-forward direction can be established utilizing density mappings indicative of frequency at which a driver looks in a certain direction.

Objects/areas-of-driver-interest can be identified by correlating the representative mapping (therefore, this can also be accomplished from the direct data of angularity) against prescribed/defined probable locations of areas/objects-of-driver-interest relative to the reference-base position.

When addressing head orientation-based analysis, the measure of gaze angularity can be derived from a sensed head-orientation-based gaze-direction vector.

In another embodiment, the invention takes the form of a method for developing a bench-mark (reference frame) for comparison in assessing driver activity and/or driver condition. This method comprises (includes, but is not limited to) collecting (which may also include using a stream of recorded data) a stream of gaze-direction data based on a sensed characteristic of a driver, and based on density patterns developed therefrom, defining gaze-direction-based parameters corresponding to at least one region of probable driver interest.

As before, this method entails utilizing measures of at least one of (1) driver ocular orientation and (2) driver head orientation to constitute the gaze-direction data.

A region representative of typical eyes-forward driving is established based on a high-density pattern assessed from the collected gaze-direction data. Exemplarily, the region may be defined as an area defined in two dimensions such as a parabola or a volume defined in three dimensions such as a cone radiating from the reference frame with an apex thereof essentially located at eye-position of a typified driver relative to an established reference frame.

The collected gaze-direction data is compared to the established representative region, and thereby identifying gaze departures based on the comparison. Based on similar comparison, other qualities of the environment or the driver may be deduced. For example, the gaze-direction data can be used to identify and/or measure such things as driver cognitive distraction, driver visual distraction, and/or high driver work load conditions.

Still further, the method contemplates and provides means for quantifying the severity (degree) of a driver's impairment with respect to performing driving tasks based upon an ascertained frequency or duration (depending on whether occurrences are discrete or continuous incidents) at which such an indicative condition as gaze departure, cognitive distraction, (3) visual distraction and (4) high driver work load is detected in a prescribed time period.

The incidents of interest can be logged, stored and/or transmitted for further analysis by a processor. Conversely, the data representative of the incidents of interest can be analyzed on a real-time basis either locally, or remotely if also transmitted in real-time.

At least one exemplary utilization of such analysis is to provide driver feedback when the severity quantification exceeds a prescribed severity threshold level. For instance, a driver may be warned when excessive levels of visual distraction (too much looking away) or cognitive distraction (not enough looking away—staring ahead when preoccupied) occur.

Another utilization of the output from the analysis is to tailor prescribed functionalities performed by the vehicle when the severity quantification exceeds a prescribed severity threshold level. An example would be causing an adaptive cruise control system to institute additional space between a leading vehicle when the driver is assessed to be distracted or inattentive.

One particularly advantageous mode for analyzing the stream of collected gaze-direction data is the utilization of a primary moving time-window of prescribed period traversed across the data series (a well known analysis tools to those persons skilled in the statistical analysis arts), and detecting characteristics within the primary moving time-window indicative of an occurrence of driver time-sharing activity. An example is taking an average of certain data within a moving ninety second window. As the window progresses along the data series, new data is added to the consideration and the oldest data is disregarded (new-in and old-out in equal amounts, based on time).

Utilization of this process can be used to identify periods of high driver workload based on a frequency of threshold-exceeding occurrences of driver time-sharing activity. In order to rid the window of the effect of the detected occurrence, refreshment (flushing or restoring to normal) of the primary moving time-window upon the detection of cessation of an occurrence of driver time-sharing activity is caused. In this way the effect of the occurrence is minimized after detection and analysis, thereby readying the system for a next departure from normal.

As will be discussed in greater detail hereinbelow, several characteristics of ocular activity can be identified based on observed eye activity. Some common characteristics easily recognized by the layperson are blinking and glances. What may not be as readily appreciated by the layperson is that such things as a glance may be characterized or identified based upon lesser known constituent eye-activities such as saccades, fixations and transitions, each of which have measurable defining characteristics.

In another embodiment, the invention takes the form of a method for automated analysis of eye movement data that includes processing data descriptive of eye movements observed in a subject using a computer-based processor by applying classification rules to the data and thereby identifying at least visual fixations experienced by the subject. These rules or characteristics are discussed in greater detail hereinbelow. Analysis is also made of gaze-direction information associated with the identified fixations thereby developing data representative of directions in which the subject visually fixated during the period of data collection that is presently being analyzed. It should be appreciated that in the presently described embodiment, the subject is not limited to a vehicular driver, but may be a subject of interest in other settings. At least one exemplary setting outside the driving environment is the area of test marketing in which differently positioned product representations are exposed to a test-subject (exemplarily on a bank of video displays) and those which catch their attention over the others can be identified. Still further, certain effects caused by the subjects perception during the observation can be ascertained from certain trackable eye activity. For instance, it could be determined how long a glance occurred thereby providing an indication of relative interest caused by a first perception.

In preferred embodiments, the applied classification rules comprise at least criteria defining fixations and transitions; and even more preferable, classification rules providing criteria to define saccades are additionally utilized.

The data is segregated, based at least partially on gaze-direction of fixations, into delimited data sets, each delimited data set representing an area/object-of-subject-interest existing during the period of data collection.

In another respect, glances are identified by applying at least one glance-defining rule to the data, each of the identified glances encompassing at least one identified fixation. In this aspect of the invention, the glance-defining rule is based upon at least one of the characteristic including: glance duration, glance frequency, total glance time, and total task time.

In another aspect, a relative density is assessed of one glance set in comparison to at least one other glance set, and based thereupon, the method identifies the represented area/object-of-subject-interest of the compared glance set.

In a similar regard, the inventive method contemplates assessing a relative density of at least one glance set among a plurality of glance sets, and based upon a mapping of the assessed relative density to known relative densities associated with settings of the type in which the eye movement data was collected, identifying the represented area/object-of-subject-interest of the compared glance set. For example, using the exemplary percentages for known dwell periods on certain objects or areas of driver interest during normal driving conditions, those objects or areas can be identified from the collected data.

In another aspect, relative densities of at least two glance sets developed from data descriptive of eye movements observed in a spatially known setting are assessed and the represented area/object-of-subject-interest of each of the two compared glance sets is ascertained therefrom. Locations of the represented areas/objects-of-subject-interest are then ascertained in the known setting thereby establishing a reference frame for the known setting because the deduced locations can be mapped or overlaid on known locations of the objects/areas.

In a particularly preferred embodiment, however, the subject is a driver of a vehicle, and based on a density of at least one of the glance data sets, an eyes-forward, normal driver eye orientation is deduced.

A further aspect of the invention in which a vehicle driver is the subject contemplates utilizing a plurality of analysis protocols, the selection of which is dependent upon prevailing noise characteristics associated with the data set being processed.

In one development, a first data filter of predetermined stringency is applied to an input stream of data comprising the data descriptive of eye movements observed in a driver of a vehicle. The computer-based processor is utilized, and therefrom, a first filtered data stream is outputted that corresponds to the input stream of data. (This concept of correspondence can be one in which each outputted value corresponds to the inputted value from which the outputted value is derived. Quality of the outputted first filtered data stream is assessed by applying a first approval rule thereto, and data of the outputted first filtered data stream passing the first approval rule being outputted and constituting an approved first stream of data.

In a further development, a second data filter is applied to the input stream of data that is of greater stringency (more smoothing to the data) than the first data filter utilizing the computer-based processor; and therefrom, a second filtered data stream is outputted that corresponds to the first filtered data stream via its common derivation from the input stream of data (again, correspondence/comparison based on having been computed from the same input data value). Quality of the outputted second filtered data stream is assessed by applying a second approval rule thereto, and data of the outputted second filtered data stream that passes the second approval rule is outputted and constitutes an approved second stream of data.

From the two approved data streams, a collective approved stream of data is composed that is constituted by an entirety of the approved first stream of data, and the collective approved stream of data being further constituted by portions of the approved second stream of data corresponding to unapproved portions of the outputted first filtered data stream.

In at least one embodiment, the first and second approval rules are the same; in another, the first and second approval rules are based on the same criteria, but may not be the same rules.

In a further development, the method comprises selecting at least two analysis protocols to constitute the plurality from a group consisting of: (1) a velocity based, dual threshold protocol that is best suited, relative to the other members of the group, to low-noise-content eye and eyelid behavior data; (2) a distance based, dispersion spacing protocol that is best suited, relative to the other members of the group, to moderate-noise-content eye and eyelid behavior data; and (3) an ocular characteristic based, rule oriented protocol that is best suited, relative to the other members of the group, to high-noise-content eye and eyelid behavior data.

In an associated aspect, the selection of protocols for any given data set is biased toward one of the three protocols in dependence upon a detected noise level in the data set. In another aspect, the rule oriented protocol considers one or more of the following standards in a discrimination between fixations and saccades: (1) fixation duration must exceed 150 ms; (2) saccade duration must not exceed 200 ms; and saccades begin and end in two different locations.

In a further regard, quality of the data descriptive of eye movement is assessed based on relative utilization of respective analysis protocols among the plurality of analysis protocols. Alternatively, or in association therewith, the quality assessment can be made considering time-based, relative utilization of respective analysis protocols among the plurality of analysis protocols over a prescribed time period.

As described hereinabove, analysis of the stream of collected driver eye-gaze data can be made utilizing a stream-traversing primary time-window of prescribed period, but in this instant, an artifact that clouds the trueness of a portion of the data stream is detected. In this event, resort is made to a secondary moving time-window simultaneously traversing the data stream and generating highly filtered data from the collected data when the artifact is encountered. A similar process is prescribed for treating detected data quality-degradation beyond a prescribed quality threshold level during data stream traversal. In this case, resort is again made to a secondary moving time-window that is simultaneously traversing the data stream, and therefrom, generating highly filtered data from the collected data when the data quality-degradation exceeds the prescribed quality threshold level. Subsequently, return is made to the primary moving time-window when the data quality-degradation is detected to have subsided within the prescribed quality threshold level.

DETAILED DESCRIPTION

Figure 1:
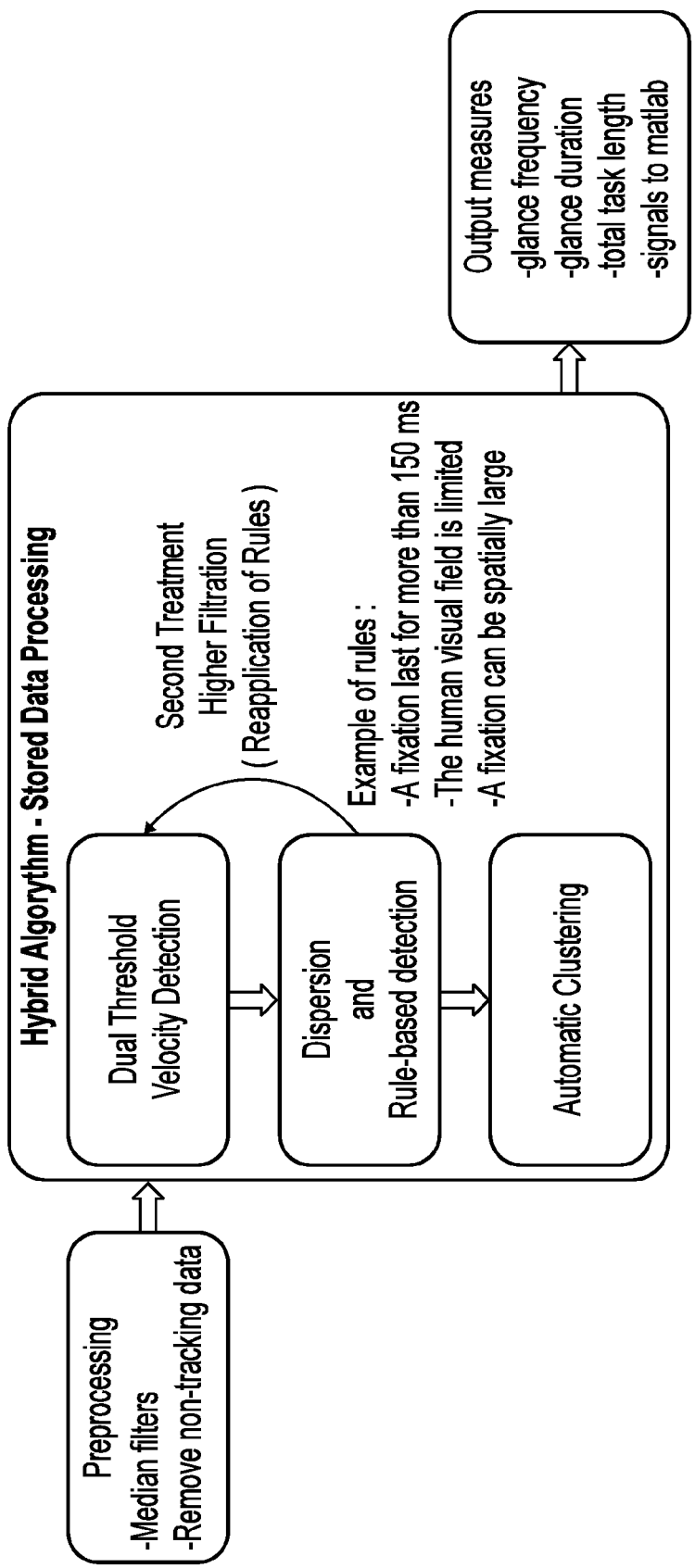
FIG. 1 is a diagrammatic illustration of and off-line hybrid algorithm.

Before the actual data treatment techniques that are the focus of the presently disclosed invention(s) are described, some basic information will be provided regarding rudimentary characteristics of eye movements, as well as some general information about typical tracking systems that can be used to sense, quantify, and optionally record data descriptive of head and/or eye orientation (location and movement characteristics) in an effort to facilitate those readers possessing less than ordinary skill in these arts.

With respect at least to eye movement-based systems, presently available sensing systems used for gathering eye movement data deliver "raw" eye-movement signals that are rather noisy and which includes artifacts. As will become evident from reading the balance of the present disclosure, typically, head orientation tracking data can be utilized as an approximation, and therefore often a valid substitute for eye tracking data. Since eye tracking data obviously almost always provides a truer indication of where the subject is looking (over head tracking data), however, it is eye tracking that is predominantly considered in this invention disclosure.

Algorithms of the present invention(s) process this information and produce output representing such things as measures of glance frequency (the number of glances toward a target area during a pre-defined time period), single glance duration, total glance time and total task time. The algorithms embody rules that are defined to trigger different warnings; for example, if the driver looks at his/her cellular for more than two seconds without looking back to the road. The defining of the exact trigger rules is the product of trimming in the real-time systems that are continually under development. Human Machine Interaction (HMI) are also considered by the inventions disclosed herein; examples of such HMI concepts have been more thoroughly described in U.S. patent application Ser. No. 10/248,798 filed 19 Feb. 2003 and entitled SYSTEM AND METHOD FOR MONITORING AND MANAGING DRIVER ATTENTION LOADS, the disclosure of which, in its entirety, is hereby expressly incorporated. Therein, concepts for how to present these warnings are presented.

Aspects of the presently disclosed inventions include two differently based algorithms; one for off-line post data-gathering processing, and one for real-time processing that takes place essentially simultaneously with the data gathering (when the quantified characteristic is being performed). They are similarly based, but the real-time algorithm has an initialization procedure and lacks some of the off-line features. A primary purpose and benefit of off-line analysis is the treatment of recorded or stored characteristic data. A primary purpose of real-time analysis is to immediately treat collected data, and make it available for essentially simultaneous utilization for such things as feedback to the observed subject, or adaptation of relevant systems such as to vehicular systems when the subject of the observation is a vehicle driver.

Concerning drivers, one of the purposes for the off-line algorithm is to analyze eye-movement data from tasks, such as changing radio station or using the RTI system (while driving), to determine how much visual demand the unit poses on the driving task. A purpose of the real-time algorithm is to determine how much the driver looks at the road. One objective of the present invention is to adapt or enable the real-time algorithm so that results similar to that from the off-line algorithm are obtainable.

Eye movements can generally be divided into two categories: saccades and fixations. A fixation occurs when the eyes are fixated on something; for instance, the letters on this page. This is also when the brain can assimilate information which is interpreted as the visual images of the thing(s) upon which fixation is focused. A saccade on the other hand is the movement in between fixations; that is, changing the point of regard. Saccades are very fast (with peak velocities at 700°/s for large amplitudes) and the viewer's brain suppresses recognition of these incidents because light is moving across the retina at these times too fast to be interpreted by the brain.

A glance towards something, for instance a mobile telephone, is a combination of a saccade away from a predefined target area (e.g. the road), initiation of the glance, and fixations at a new target area (e.g. the mobile telephone). The glance is terminated when a new saccade away from the second target area is initiated. Successive saccades and fixations within the same target area are defined as part of the same glance.

Certain of the goals and advantageous aspects of the present invention(s) can be summarized as: (1) The hybrid algorithm, even at the level of just combining velocity and dispersion based algorithms, is new especially when combined with ocular rules. Heretofore, the physical capabilities of the eyes have not been taken into account when segmenting eye-movements; (2) The idea and procedure to localize the road center area using the density function peak as its center that is more detailed than merely designating the mean value of the "mountain;" (3) The algorithms, as a whole, and the way each different algorithm part cooperates with the others. The concepts of Percent Road Center (PRC) and Absolute Percent Road Center (A-PRC) as measures of driver attentiveness.

The algorithms are not only intended to produce the described measures, but can also be used to determine all measures defined in the ISO 15007-2, as well as the measures in the SAE J-2396.

Oculomotor concepts are well studied; generally, ocular motion is divided into several different categories that may be exemplified as saccades, microsaccades, smooth pursuit, vergence, tremor, drift, and the like. For purposes of the present invention, however, ocular motion is divided into two fundamental categories: saccades and fixations. The rational of the present invention is that all data points that are not saccades, are fixations. This includes smooth pursuits, which occur frequently during driving, in the fixation conception described hereinbelow.

Figure 6:
FIG. 6 is a graphic view of details of two eye movements demonstrating a micro-saccade, drift and tremor.

Fixations are defined as pauses over informative regions where the eyes can assimilate information. To be a valid fixation, the pause has to last for at least some 150 ms, the same being about the time the human brain needs to utilize the information. Although it is referred to as a "fixation," the eyes still move, making micro movements like drift, tremor and micro-saccades while "fixed" on the area. These small movements are of very low amplitude and are part of what defines a fixation. FIG. 6 represents a typical fixation with drift, tremor and a micro saccade. Therein, activity of a subject's two eyes are graphed, one above the other; time is charted on the horizontal axis, while distance is represented on the vertical axis. These movements are fortunately either very slow (typically on the order of 4 and 200 s$^{-1}$) or very small (typically on the order of 20 40 inches), which prevents their detection by typical equipment used in these types of applications. This is a benefit, because these deviations would other-wise be viewed as noise.

Figure 7:
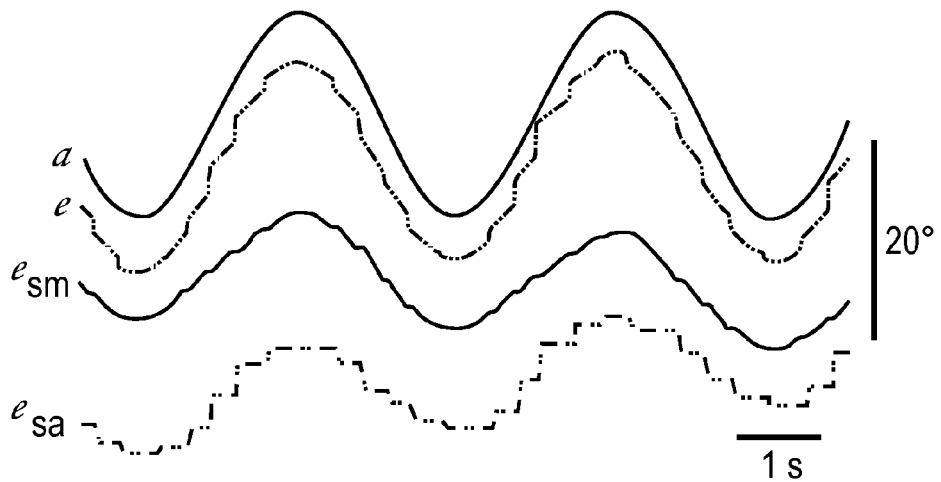
FIG. 7 is a graphical demonstration of different component characteristics of an eye movement sample.

Other larger movements, but still with sub-saccadic velocities, are termed smooth pursuits. They are a subcategory of a fixation; that is, a fixation on a moving target or a fixation on a stationary (or moving) object while the observer is in motion. When we track a target, the eyes use small saccades to bring fovea on to the target, then slower, continuous movements are performed that track the target, and are dependent upon its speed. The slow movements, with velocities ranging roughly between 80 and 160 degrees per second, constitute smooth pursuits. This behavior is shown graphically in FIG. 7 were a subject is tracking a point moving on a sinuous path represented by the curve (a). The curve (e) represents the entire eye-movement, including saccades and smooth pursuits. The curve ($e_{sa}$) represents the removal of smooth pursuits, and ($e_{sm}$) shows the curve with saccades removed. In general, the entire tracking behavior is referred to as a smooth pursuit and can be considered to be a drifting fixation. For this reason, this type of behavior is referred to herein relative the present invention(s) as a fixation due to the fact that information is being processed during this movement and the saccades are two small to be detected with available eye-movement tracking systems.

Saccades are rapid eye movements that occur as a person's view changes between two points. Saccadic movement varies in amplitude, duration, velocity and direction. The duration of saccades larger than about five degrees in amplitude will be about 20-30 ms; thereafter, about two milliseconds can be added for every additional degree. Peak velocities typically range from some 10 degrees per second for amplitudes less than 0.1°, to more than 700 degrees per second for large amplitudes.

Figure 8:
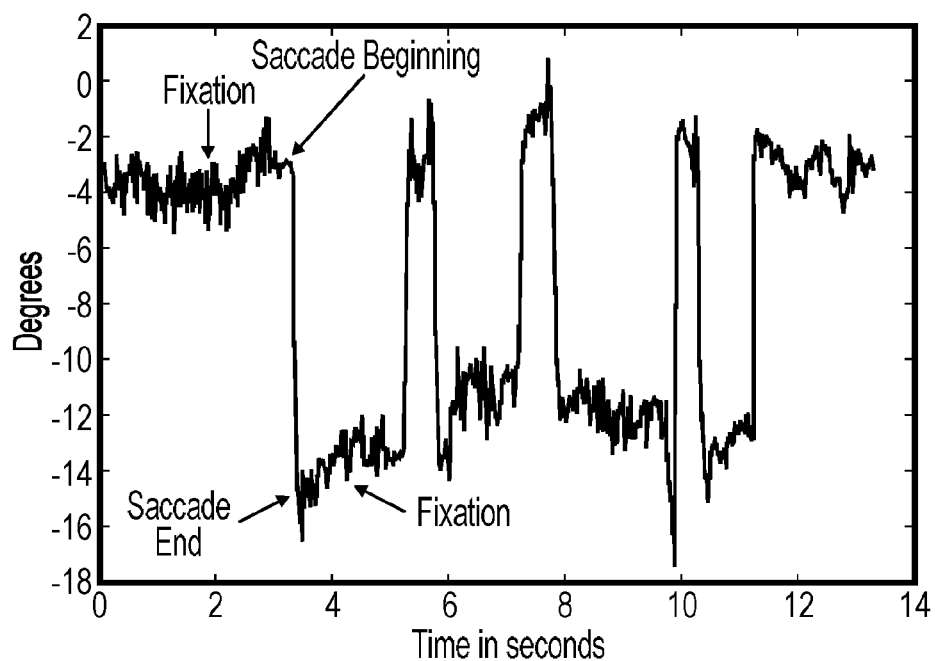
FIG. 8 is a graphical depiction of a plurality of fixations and saccades.

Typical saccades from one point of regard to another are shown in FIG. 8, which depicts an example of a good tracking measurement with virtually no noise. An exemplary saccade is shown beginning at point (A) and ending at point (B). Also, the illustrated eye movement only consists of movement around one axis; that is, no saccades were measured in the horizontal plane.

During saccadic movement, the human brain generally does not perceive information since light is moving too fast over the retina. It should be appreciated, however, that it has in fact been shown that some information is actually being processed during saccades. Recognized perception only occurs if an observed object is moving at the same speed and in the same direction as the eyes. The general absence of information forces the brain to make a calculation of amplitude and duration in advance. Inaccuracy and noise in this process almost always generates an over- or under-shot on the order of some degrees. This is corrected by drift or a new saccade that is much shorter than the previous, and therefore more precise. Here, a saccadic undershot represented by the long vertical portion of the trace (A) is corrected by the shorter vertical portion representing a corrective mini-saccade (B). Such a corrective saccade is often of such low amplitude that it is undetectable using known eye-tracking machines, and is considered instead as added noise.

Apart from these three kinds of movement, there is a different kind of visual behavior commonly referred to as blinks. Humans normally blink about once every two seconds; a characteristic that has a devastating impact on gaze estimation. During the actual closure of the eyes during a blink, gaze cannot be measured and since blinks do occur during both saccades and fixations, it is hard to anticipate where the eyes will be looking when again visible to the tracking machine. Fortunately, blinks are very fast; on the order of 200 ms for an entire blink. This means that the eyes are totally occluded for only about 100-150 ms. Because subjects are generally totally unaware of the occurrence of blinks, the present invention achieves a more coherent and stable perception of reality by suppressing the recognition of both saccades and blinks.

Properties of the eyes work in favor of segmentation, meaning there are physical boundaries for ocular movements that provide rules for classification. For example, one saccade cannot be followed by another with an interval less than some 180 ms; this means that it is unlikely for a saccade to last for more than 200 ms. A 200 ms saccade would have an amplitude of about 90 degrees which is very uncommon. Still further, any measured saccade that is longer than about 220 ms is more likely to be two saccades, with one fixation in-between. Another interesting fact is a subject's suppression of blink recognition mentioned above. Subjects are generally unaware of the occurrence of blinks, and therefore can generally be removed from the analysis since eye behavior is not affected by their occurrence. The following constitute physical boundaries of the eyes that are relevant to the present invention(s): fixations last for at least, about 150 ms; a saccade can not be followed by another with an interval less than some 180 ms; the human visual field is limited; a fixation can be spatially large (smooth pursuit); saccades are suppressed by the visual center; blinks are suppressed by the visual center.

For the Driver of a vehicle there could be even more restrictions such as: it is not likely to find fixations on the inner ceiling or on the floor during driving, especially not during a task; a significant proportion of a subject's attention (and fixations) are likely to be found on the center of the road and smooth pursuit velocities are low to moderate. As an example, oncoming traffic and road signs trigger most measured pursuits. In the present invention, these boundaries are used to define a framework that can be used as a part of the segmentation of driver eye movements.

According to the present inventions, ocular measures are divided into two groups, glance based measures and non-glance based measurers. These two groups are formed by the outcome of a basic ocular segmentation where fixations, saccades and eye-closures are identified.

As intimated above, different researchers have different methods of analyzing data and defining fixations/saccades. Having uniform rules and benchmarks are important so that all such analysis methods can be based on a generally accepted international standard. This is why the measures in this work are based on the definitions in the ISO 15007-2 and SAEJ-2396 standards. They both standardize definitions and metrics related to the measurement of driver visual behavior, as well as procedures to guarantee proper conduction of a practical evaluation. The SAE document depends on many terms of the ISO standard, and each works as a complement to the other.

In the course of describing the present invention(s), equipment and procedures are identified that are suitable for both simulated environments, as well as for on-the-road trials. Both standards (SAE and ISO) are, however, based on a video technique utilizing, for example, camera and recorder, with manual (off-line) classification of fixations and saccades performed by human raters. The manual video transcription is a time consuming and potentially unreliable task. Therefore, an automated method such as that upon which the present inventions are based, is preferable. The incorporation and exemplary reliance on the ISO/SAE-type measures can be advantageously relied upon using any system that classifies eye movement, either manually or automatically.

Following, three subsections of basic ocular segmentation are described, as well as two groups of measures. Basic ocular segmentation divides eye movements into the smallest quantities measurable with available eye-tracking systems. These eye-movement "bricks" represent a base from which all glance-based and statistical measures are derived. In summary, they include: (1) saccades that define the rapid movement occurring when looking from one area of interest to another; (2) fixation which addresses alignment or steadiness of eyes position so that the image of the target upon which fixation is being made falls on the fovea for a given time period; (3) eye closures where short duration eye closures are referred to as blinks and long eye closures may be characterized as drowsiness.

Figure 9:
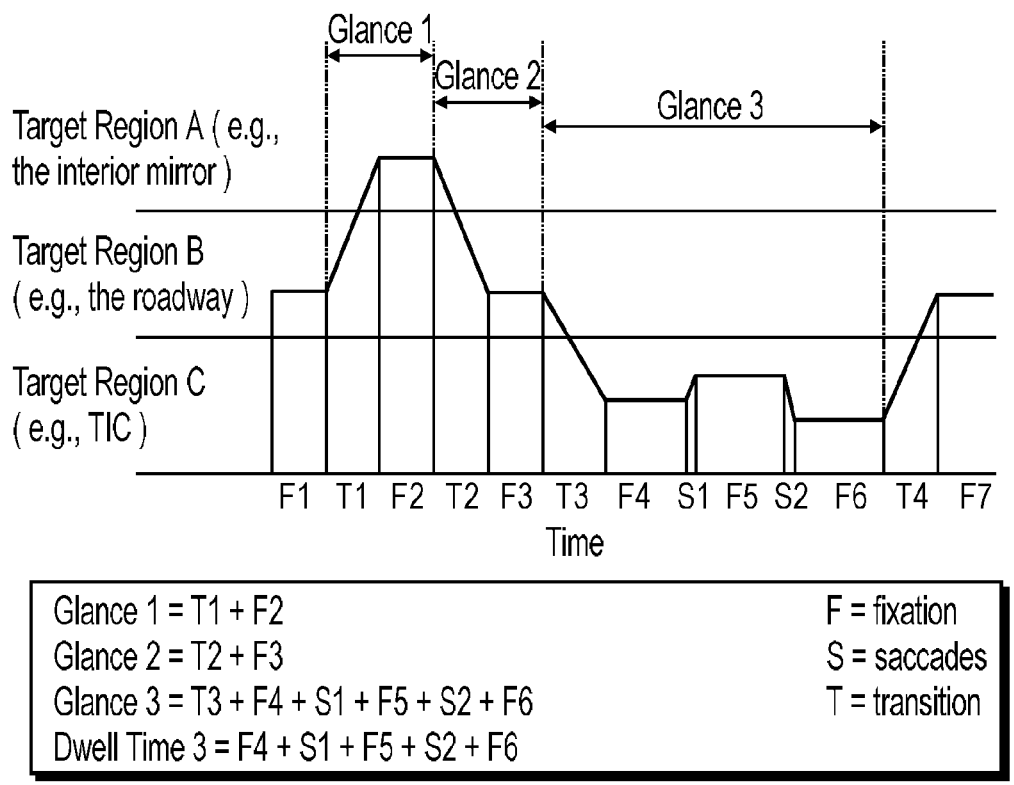
FIG. 9 illustrates eye movement components that constitute glances.

In order to comprehend the measures utilized in the ISO/SAE documents, it is important to be familiar with the definition of a glance, which by SAE standards, is considered as a series of fixations at a target area until the eye is directed at a new area. For example: if a driver initially looks straight-ahead (on the road) and then to the radio, fixating first on the display and then the volume control, he or she performs two fixations (not counting the first one straight-ahead) and two saccades, all of which compose one glance. The glance is initiated as the first saccade away from the road begins (this saccade is called a transition) and terminated as the last fixation at the radio ends. FIG. 9 provides a graphic illustration of the components of a typical driver three-glance series. Therein, fixations, saccades and transitions are quantified as components of the several glances.

All glance-based measures are derived from these definitions and are to be considered a "higher-level" description of eye movements that constitute the "bricks" described in the previous section. These measures reflect different properties such as time-sharing, workload and visual attention demand. The measures defined and utilized in the ISO and SAE protocols are: (1) glance duration defined as the time from which the direction of gaze moves towards a target to the moment it moves away from it. Rather long durations are indicative of a high workload demand in that area; (2) glance frequency defined the number of glances to a target within a pre-defined sample time period, or during a pre-defined task, where each glance is separated by at least one glance to a different target. This measure should be considered together with glance duration since low glance frequency may be associated with long glance duration; (3) total glance time defined as the total glance time associated with a target. This provides a measure of the visual demand posed by that location; (4) glance probability defined as the probability for a glance to a given location. This measure reflects the relative attention demand associated with a target. If calculated over a set of mutually exclusive and exhaustive targets such a distribution can be used to make statistical comparisons; (5) dwell time defined as total glance time minus the saccade initiating the glance; (6) link value probability defined as the probability of a glance transition between two different locations. This measure reflects the need to time-share attention between different target areas; (7) time off road-scene-ahead ("road scene ahead" excludes the rear view and side mirrors) defined as the total time between two successive glances to the road scene ahead, and which are separated by glances to non-road targets; (8) transition defined as a change in eye fixation location from one defined target location to a different i.e. the saccade initiating a glance; (9) transition time defined as the duration between the end of a fixation on a target location and the start of a new fixation on another target location. Since there is very little or no new information during transitions, increased transition time reflect reduced availability for new driver information; (10) total task time defined as total time of a task which is in turn defined as the time from the first glance starting point to the last glance termination during the task.

Non-glance based measures are all other measures that can be calculated other than those that are defined in the ISO/SAE standards. Two examples include: (1) mean value and standard deviation of fixation position within different clusters, for example, the road scene ahead and a cellular telephone; and (2) mean value and standard deviation of fixation dwell-time within different clusters and/or different tasks. These types of measures are interesting when analyzing, for example, normal driving compared to driving during high cognitive load periods such as would occur if a driver were to be involved in a mathematic task.

A general objective of the present invention is to provide a robust automation of the data analysis of eye movements with focus on the measures prescribed in the ISO 15007-2 and SAEJ-2396 methods for measurement of driver visual behavior with respect to transport information and control systems. Exemplary tools utilized in the present automation include eye tracking systems that are otherwise discussed in greater detail herein. Advantageously, the algorithms and implementing systems should only require a minimum of human interaction, such as loading/saving data and visual inspection of detected clusters and outliers.

A starting-point for the present disclosure was a showing that an automated analysis is possible using available sensing system; the particular study revealed high correlations on all measures. In this example, the signal was filtered using a sliding thirteen-sample median window filter to reduce noise, eliminate some outliers and blinks. A velocity threshold algorithm was developed to differ saccades from fixations (smooth pursuits were considered to be fixations) and a manual delimitation of clusters provided a base for glance classification. The procedure required significant operator input and attention; for instance, the signals had to be filtered, and outliers, short fixations, and other artifacts were manually identified. As the inventions have evolved to the point of the present disclosure, these operator-time intensive procedures have been eliminated.

Originally, the median filter width was not optimal for all subjects; the length needed to stand in proportion to the noise level. Responsively, different filter types and parameters were utilized. Also, it was learned that the velocity algorithm was sensitive to noise. Hence, the threshold was set to 340 degrees per second that is substantially above saccadic start and ending velocities. To compensate for this, the two samples preceding and following a saccade were also marked to have saccadic velocities. Since saccades vary in amplitude and peak velocity, so does their acceleration. Thus, this precursor method provided a good approximation of saccade beginnings and endings, only. Therefore, an objective of the presently evolved invention is to provide a robust technique for saccade/fixation identification that is more accurate.

Furthermore, a need for a clustering technique that automatically identifies glance target areas and glances was identified. An objective was to eliminate outliers and other artifacts in an automated way, other than by the traditional means of human rating.

An understanding of the origin and properties of the data disclosed herein is important when designing detection algorithms. Therefore, the available data and the technical platforms used to obtain that data are described.

Regarding the invention(s) at hand, FIG. 1 of the accompanying drawings provides a general overview of an exemplary off-line analysis algorithm. Raw eye movement data is input at the upper left-hand box where pre-processing is performed. Exemplarily, such pre-processing includes a median filter that subdues noise, artifacts and blinks. Also, all non-tracking data is removed at this functional station.

The large, intermediate box, represents an exemplary algorithm that as illustrated, is a hybrid treatment between two commonly used data-treatment-algorithms (Dual Threshold Velocity Detection and Dispersion and Rule-Based Detection). As indicated in the right-portion of the intermediate box, the applied ocular rules are based on known limits or parameters of certain aspects of ocular behavior such as minimum length (with respect to time) of a fixation generally defined by human ocular capabilities. The bottom box inside the hybrid algorithm represents an adaptive clustering algorithm that clusters fixations, based on one or more characteristics thereof, and in practice makes the clusters tend to "float" into place as the number of sampled glances increases.

Figure 3:
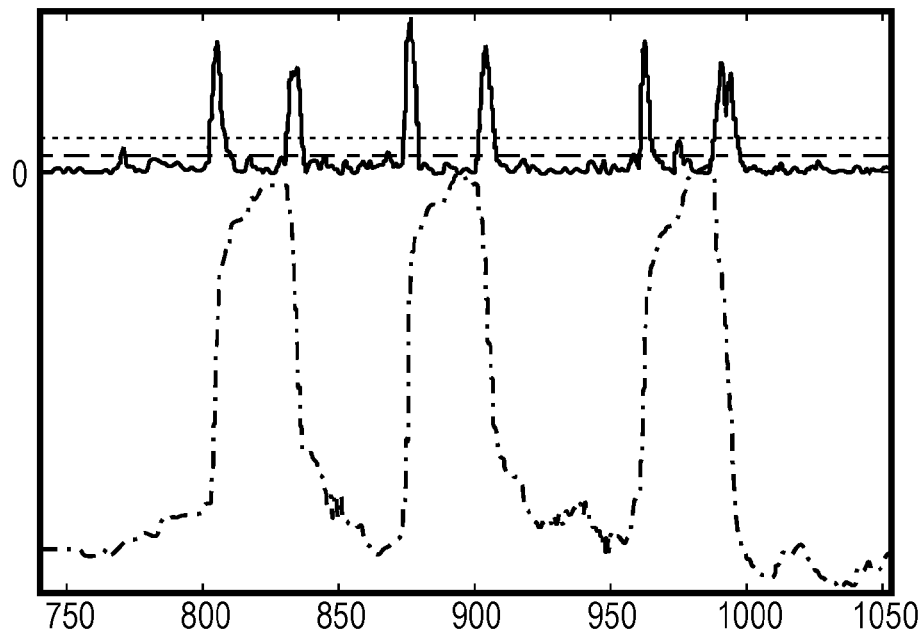
FIG. 3 is a graphic view demonstrating threshold rules that define fixations and saccades.

The Dual Threshold Velocity Detection algorithm represented by the upper box inside the hybrid algorithm is based on eye movement velocity (degrees/second). Referring to FIG. 3, a high threshold (top, flat, dotted line) differentiates fixations between those that have low velocities, from saccades. The lower dot-and-dash curve represents an actual eye-movement, illustrated in one dimension, and the solid peaked curve represents the derivative thereof, or eye-movement velocity. Once a saccade is detected, a low-threshold (short-and-long dashed line) is applied to determine the start and ending points. The reason to use two thresholds is to avoid noise triggers caused by saccade detection. It should be appreciated, however, that as noise increases, so does the error in this protocol.

In addition to saccade detection, a dispersion protocol is used in conjunction with applied ocular rules. The rules determine when detected saccades and fixations are not natural; that is, their defining data is in some way outside of accepted characteristic parameters for the assigned classification (saccades and fixations).

Examples of such rules could be that a fixation has to last for more than 150 ms and a saccade is measured by some predetermined shorter period. Also, a saccade cannot return to the same area from which it started. Whenever these rules are applied to change a fixation into part of a saccade or a saccade into part of a fixation, the dispersion algorithm determines how the situation will be handled. For example, if two successive fixations at the same target are detected with a 60 ms saccade in-between, it can be deduced that it might have been noise that triggered the saccade detection. Whether it is noise or not is determined by the dispersion protocol. If the two fixations are within a certain distance from each other (the dispersion threshold), they are a part of the same fixation, and the saccade is changed into part of that fixation, otherwise it is most probably a correct detection.

Figure 4:
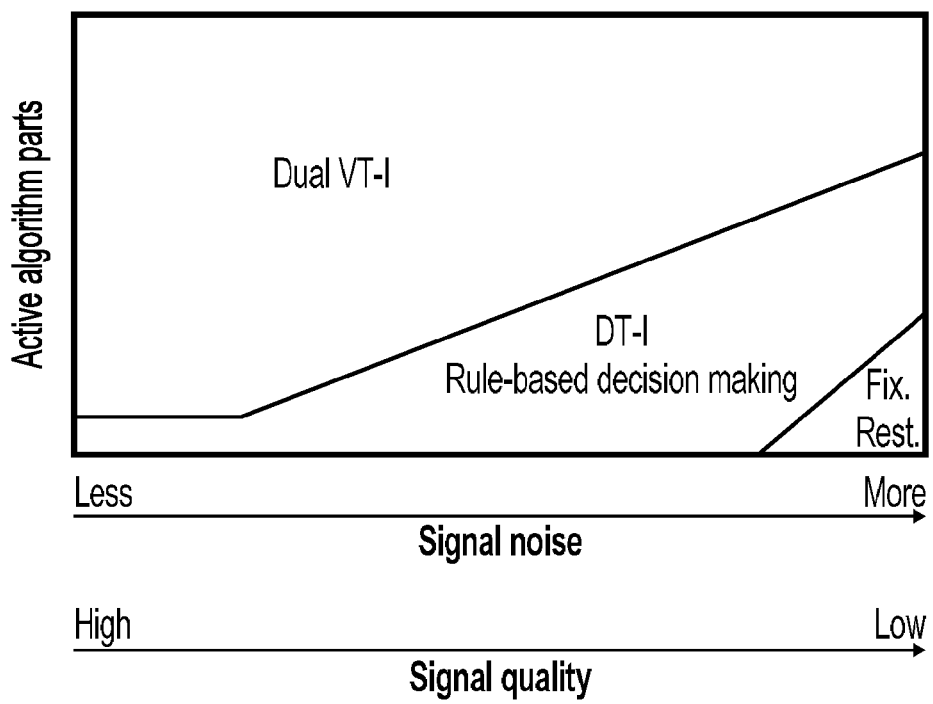
FIG. 4 is a diagrammatic illustration demonstrating analytical tool choice based on signal noise quantity.

A main precept of the hybrid algorithm is that it automatically biases the "decision" as to which treatment algorithm (or parts thereof) will be applied to the data based on the current noise level. As depicted in FIG. 4, relatively noise-less tracking data that is of higher quality will be treated predominantly using Dual Threshold Velocity Detection. The presence of an average or intermediate amount of data noise/quality increases the influence of the Dispersion Detection treatment of the data. Finally, and as represented at the right-side of FIG. 4, fixation restoration can be affected when the data is very noisy and of low quality. Usually such low quality or noisy data will only be a transient effect and not apply to the overall data stream. In the event that portions of the data are of such low grade quality, restoration of that portion takes place by applying a stringent filter to the corresponding data to see if it can be "calmed" (smoothed) enough to discern the behavior underlying the extreme noise. The restoration is accomplished by a "substitution" of the heavily treated portion when the more stringently filtered output passes the "validity" rules that the more mildly filtered data failed.

When the detection of all fixations and saccades has been finished, the data is input to the clustering algorithm that identifies glances based on the outcome of a performed cluster analysis, exemplary details of which are developed more fully hereinbelow.

Figure 2:
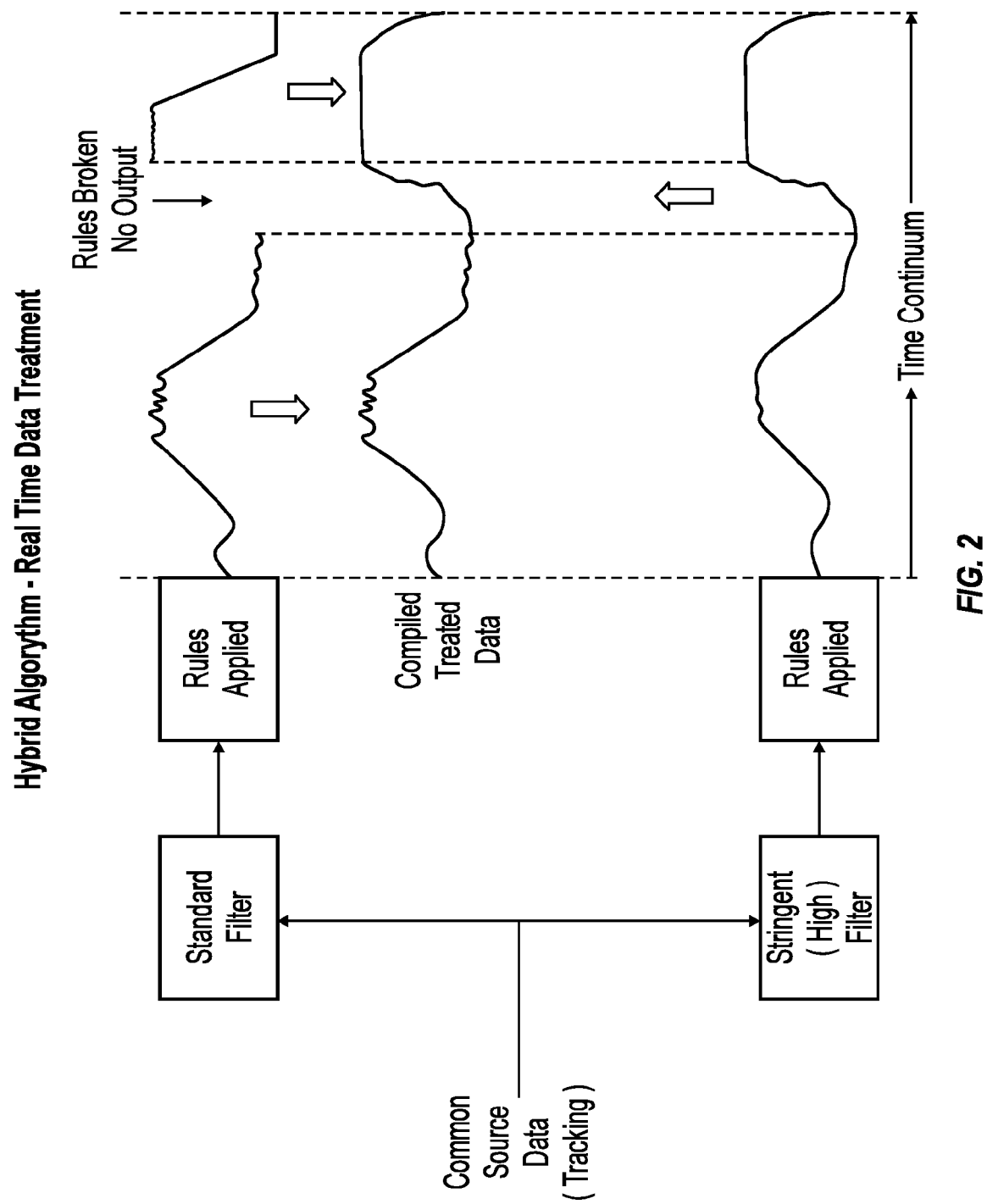
FIG. 2 is a diagrammatic illustration of and on-line hybrid algorithm.

FIG. 2 depicts a hybrid algorithm that is utilized to perform real-time tracking data treatment. Raw tracking data, typically in any data-stream form, is obtained from a sensory system regarding head and/or eye orientations and movements. Because the processing is taking place on a real-time basis, the luxury of being able to recycle the data for any further filtering pass if it fails to meet rule criteria is not enjoyed. Best possible data must be made available at all times. Therefore, the real-time hybrid algorithm essentially runs two tandem treatments of the same data. As depicted in FIG. 2, the source data is treated above using a standard filter and simultaneously, in parallel below, using a more stringent filter. At the same time, the differently filtered source data is treated with a rules set. Usually the rules that are applied to each filtered data stream are identical, but each might be tailored depending upon the respective filtration characteristics.

From each of the two rule treatments, a data stream is produced. As may be appreciated from FIG. 2, the character of the two outputted, filtered streams is different. Preferably, the standard filter has been quite mild with respect to smoothing the data, and the rules set applied to the data stream endeavors to determine whether or not a valid fixation or saccade is occurring. If the rules cannot be met, then no data stream is outputted. This blank in the data may be appreciated in the top, right-hand corner of FIG. 2. It is possible that simply too much noise is present in the portion of the stream of data that fails to meet the applied rule(s).

During this entire time, the data is also being processed with the stringent filter as described above. Typically, the stringent filter does significantly "smooth" the data in an effort to remove noise. The outputted data may be less sharp, but when the same rules are applied to the more highly filtered data that corresponds to the blank zone, non-rule compliant standardly filtered data portions, saccade or fixation characteristics are discernible. When that is the case, the rules are passed, and valid characterization of the data is obtained. This rule-passing portion of the highly filter data corresponding to the blanked-out, rule breaking lesser filtered data zones is merged into the outputted stream that has passed after standard filtration. This is illustrated as the compiled treated data stream in FIG. 2.

The compiled data stream, while possibly having short blank portions where neither of the differently filtered data streams passed the applied rule(s), is substantially contiguous if the source data is of acceptable quality (lack of noise) in a general sense. That is to say, very low-quality data will never be acceptable, and cannot typically be filtered or treated to be made acceptable. But where the source data is generally acceptable except for certain sub-standard portions, the exemplary hybrid algorithm for treating real-time tracking data produces an outputted stream of compiled data composed of classifiable fixations and saccades suitable for further processing, such as cluster and density analysis as is described in greater detail herein.

Figure 28:
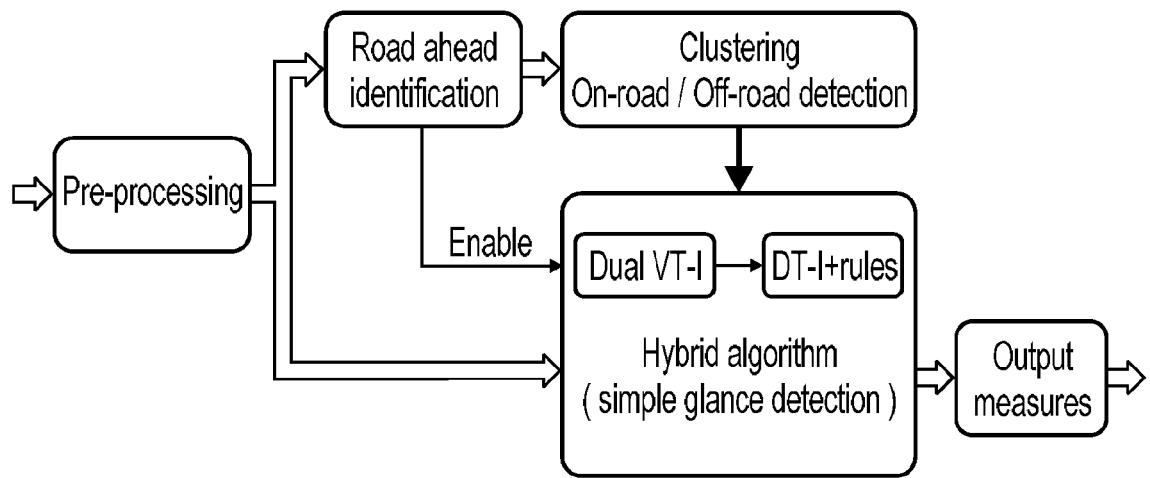
FIG. 28 is a diagrammatic view of an alternative arrangement for affecting real-time analysis of orientation data.

FIG. 28 provides an alternative representative schematic of the real-time algorithm relating pre-processing of data, road-ahead identification, clustering and application of an hybrid algorithm which all together ultimately yield meaningful output measures.

Figure 5:
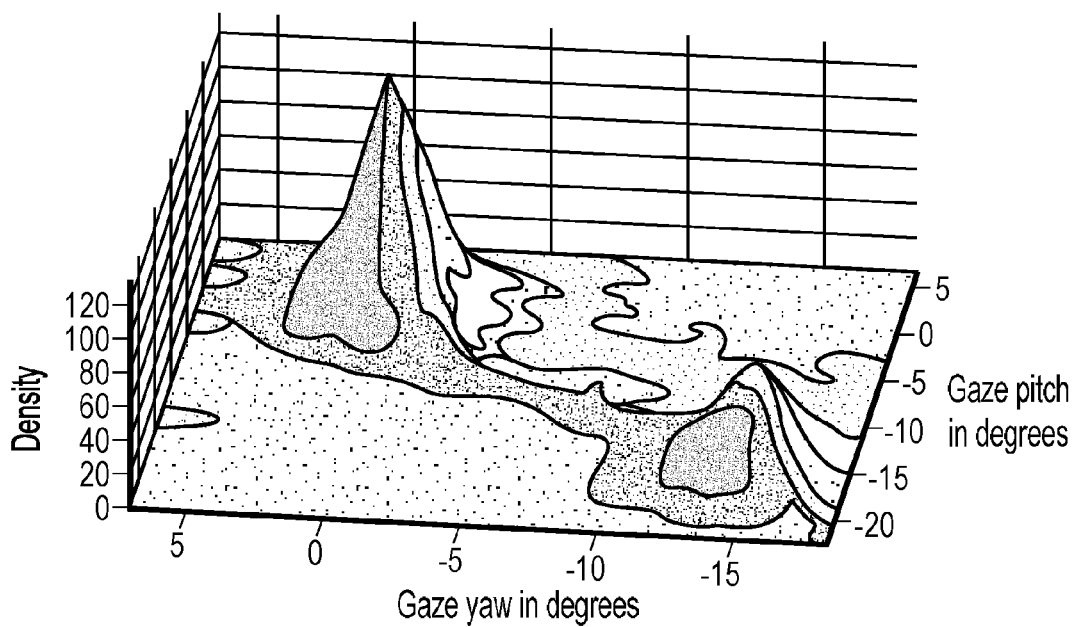
FIG. 5 is a graphic view showing two areas/objects of subject interests based on cluster or density of fact.

In this configuration, the data treatment process begins with an automatic initialization that finds what is defined as the road-scene-ahead. This is done by forming a density surface, where the time the driver looks in a certain direction is described by the gaze density in this area. For example, the more the driver looks at an area the more the gaze density will increase in that area. Most of a driver's attention is likely to be found in what is termed the center of the road-scene-ahead; there will be a "peak of attention" in the center of this area as illustrated in FIG. 5. In this illustration, the plane from where the two peaks rise should be taken to be perpendicular to the driver's face when facing the windscreen. The high peak represents the road-scene-ahead and the lower peak represents a point of concentration. In the mapped example, the subject had been asked to change the language on a Navigation system, which is what the lower peak represents.

During driving, the high (left) peak gradually builds up, and after approximately two minutes, the peak road center (PRC) position is stable. The road center area is defined as the base of this mountain and the peak as its center. The base is considered to be the 95% confidence values calculated based on the approximation that the mountain has a Gaussian shape and the mean value is the peak position. Once this has been done, glances away from the road-ahead position can be detected, and thus attention and driver workload might be calculated using the definition of peak road center as described hereinbelow.

Figure 10:
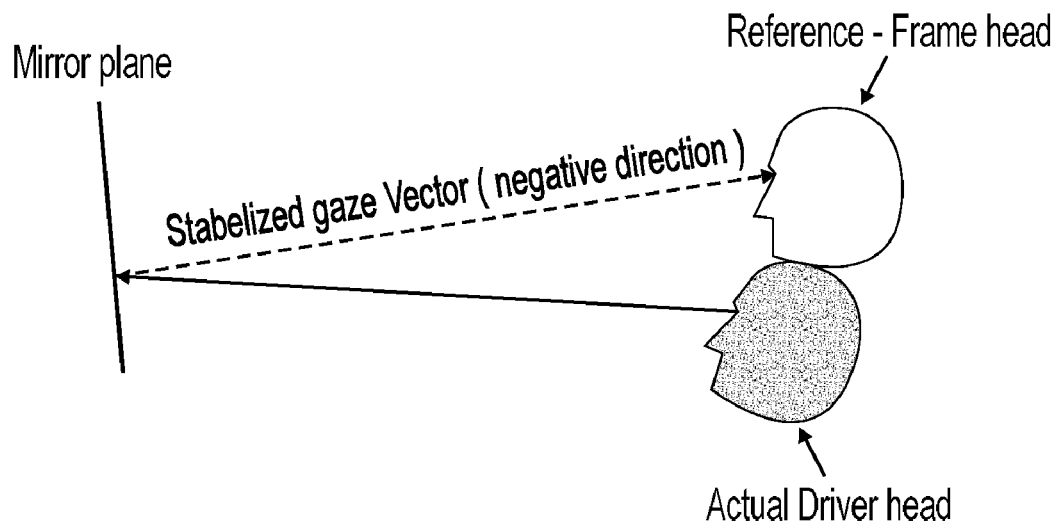
FIG. 10 is a schematic demonstrating the translation of an actual head position to a reference frame.
Figure 11:
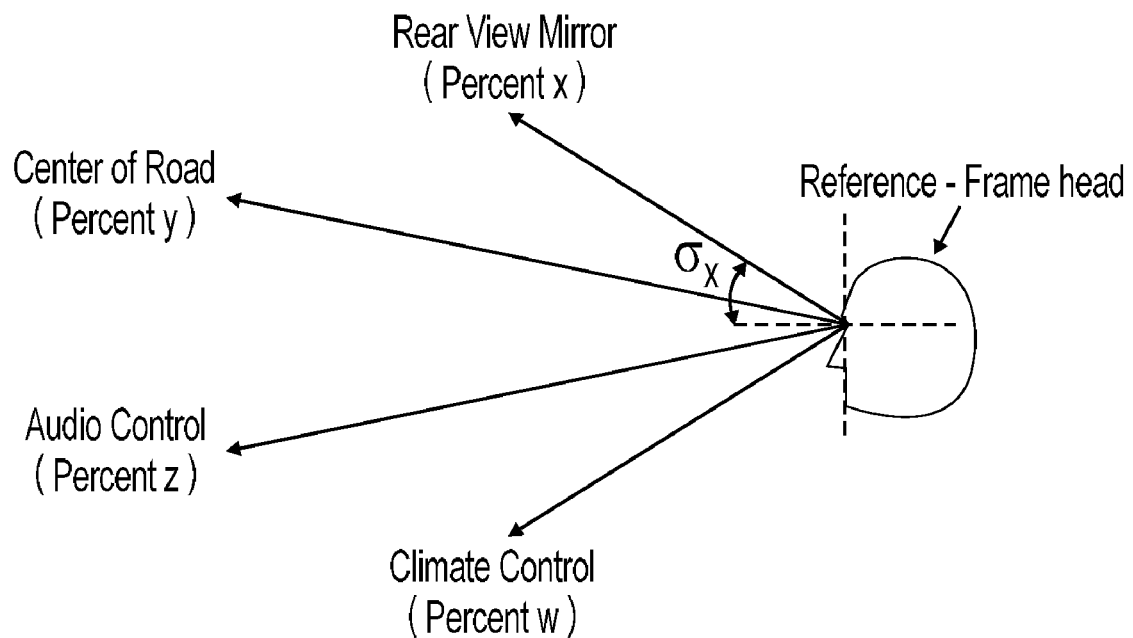
FIG. 11 is a schematic view demonstrating a measure of gaze-direction.

In a further development of the concept of identifying the road center, pre-processing of the data is performed utilizing pure mathematical translations and rotations, as well as signal filters. Since eye-gaze is a vector that originates from a point between the eyes, it becomes dependent on the position of the head. Every object in the driver's field of view can be positioned by a visual angle from the driver's eye. The angle though is highly dependent on the driver's head position and rotation, which in turn is dependent on the driver's height and preferred driving position. Different head positions/rotations affect the properties of the gaze signal as well as head movements. In order to minimize these effects, the head position is normalized to a reference position, advantageously taken as approximate mean position of most drivers. This is accomplished via a theoretical mirror plane located in front of the driver as depicted in FIG. 10.

Therein, measured gaze and head angle is projected via this plane onto a static or reference head. In this embodiment, it is the static head's gaze and head angle that is used in the algorithms.

When gaze confidence is low, for instance when the eyes are occluded, the algorithm automatically switches over to head orientation and uses the face-forward pointing direction as if it was the gaze vector. The resulting signal is then feed into the hybrid algorithm described herein, and road center is localized via the gaze density function. The initialization procedure takes approximately twenty seconds of normal driving with a speed greater than 70 km/h. In this particular application, road center was defined as an oval, 20 by 40 degrees, centered by the density function estimate of the straight ahead view. The road center geometry could, however, be dependent on speed and/or environment.

The oval described above is ideal for speeds above 70 km/h and below approximately 120 km/h on two-lane motorways with medium traffic. Other geometries can work best for some environments, travel being under-taken at different speeds, and for other applications. Measures of long glance duration; that is, one glance extended in time, seems to work better with a horizontal band of 20 degrees, centered vertically by the gaze density function.

The road center defines the only world object in the driver view. The driver either looks at the road center, or not. A transition delay is used in order to avoid a flickering signal when gaze is right on the edge of road center. Gaze has to remain constant on one of the two objects (on or off road) for more than 100 ms for a transition to be recorded.

Once road center is valid (i.e. the gaze density function is stable), PRC (taken here to mean either peak-road-center, or percentage-road-center) will start to calculate. Out of necessity, the algorithm pauses whenever there is no source tracking data. Still further, and preferred embodiment, the algorithm is disabled whenever the vehicle speed falls below 65 km/h. This also resets the value of the PRC to 80 percent.

In one version of the PRC algorithm, a maxPRC parameter prevents PRC from climbing above 80 percent. This is a simple way to stabilize PRC during normal driving (for some subjects normal driving varies between approximate PRC values of 75 and 85 percent. Using this restraint, PRC will always fall to a certain level (from PRC 80%) for a certain number of glances. The same reasoning goes for minPRC and cognitive distraction.

A shorter PRC window (3-10 seconds) is used to indicate time-sharing behavior; i.e., multiple glances between two target areas. The time-sharing behavior indication is used to reset PRC to 80% when the behavior is ended; e.g., at the end of a secondary task.

Three different warnings/feedbacks to the driver can be exemplarily given. Even if PRC falls below a threshold, the warning is not given until the driver looks away from the road (the cognitive warning is an exception of this). In the case of visual distraction, a tickle level is reached when the subject is slightly distracted; i.e., when PRC falls below 65%. The warning is given a maximum of two times during a 10 second period, and only when the driver looks away from the road; that is, the warning will be given the first two glances away from road-center after PRC has fallen below 65%. Another warning level is reached when the subject is severely distracted; i.e., when PRC falls below 58%. In this case, immediately after this warning is issued, PRC is reset to normal driving; i.e., 80%.

In the case of cognitive distraction, the cognitive warning is issued when the driver is cognitively distracted; i.e., when PRC is above 92%. PRC is then reset to 80. A long glance (away from the road) warning is issued whenever a glance outside of road center lasts more than four seconds.

Using a time window might not be the optimal solution. A one-minute time window has a one-minute history, thus what the driver did half a minute ago will affect PRC, as well as the current task. If the driver tunes the radio and thus has four glances to the radio, he will be punished by these four glances for at least half a minute; that is, PRC will remain low for at least 30 seconds even though the driver is back to normal driving (this is assuming that the task lasted for a maximum of 30 seconds). There are several ways to deal with this problem.

One is to use a shorter window with a dampening factor (to obtain the approximately same window dynamics). Another is to flush the window whenever a task is completed. Still further, a much shorter time-window, for example 3-15 seconds, can be used to decide weather a task is being performed or not.

The time-sharing detector may be used to decide weather the PRC-Sum (usually the total time of all on-road-center glances within the time window) should neglect on-road glances; that is, while performing a task, the PRC-sum decreases proportional to the off-road-center glance time, but neglects the on-road-center glance time and thus gives the same dynamic of the sum as the window would.

Another problem with the current algorithm is that blinks quite often are interpreted as glances down towards the instrument cluster. Standard data filtration will not filter out blinks due to slightly different properties in the gaze signal. Proposed solutions include using the eye-opening signal to determine weather it is blink or a glance. This requires the eye-opening signal to be present in the log data when the program is in "non-latency mode." An alternative is to design a blink detector. A blink is too short to be a glance and could thus be stopped in a filter. This will, however, introduce a delay in the system of at least 150 ms.

The algorithm above is tuned for medium traffic motorway driving at approximate speeds of 70-120 km/h. There are several ways to adapt the algorithm to different speeds and environments. One is to adapt the road-center area to speed and environment. As speed decreases, road-center will increase in size, mostly in the horizontal field. Road-center is increased so that normal driving in this speed and environment has an approximate PRC of 80%. There are two ways to do this. One is to adapt to each driver on-line. Another is to provide pre-defined road-center geometries for different speeds and environments. Still another is to adjust the warning thresholds according to the PRC level of normal driving for the particular speed and environment. Yet another is to provide a description of the environment, or at least the environment indicated by the driving behavior.

A limitation is that the algorithm will fail if the driver's head is turned more than about 60 degrees away from the road center; that is, if the driver looks over his shoulder or to the side to see if there is a car in the adjacent lane. Pattern recognition may be used to fill in those blanks.

Apart from direct warnings, PCR can be used to enable/disable a third party system or set it into different modes. For example, PRC can be used to set a forward collision warning (FCW) system into "sensitive" mode, and the instant eyes-on-road-center signal can be used to decide weather a warning should be enabled or not. It could also be used to adjust the time-gap for an Adaptive Cruise Control (ACC) control loop (increase or decrease the safety distance) or enable/disable other warnings and systems.

Figure 12:
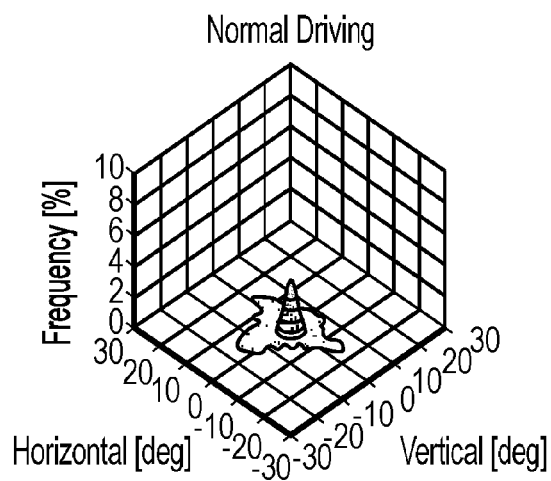
FIGS. 12-15 variously demonstrate, graphic depictions of day cluster or density collection exemplarily identifying percent or peak road-center.
Figure 15:
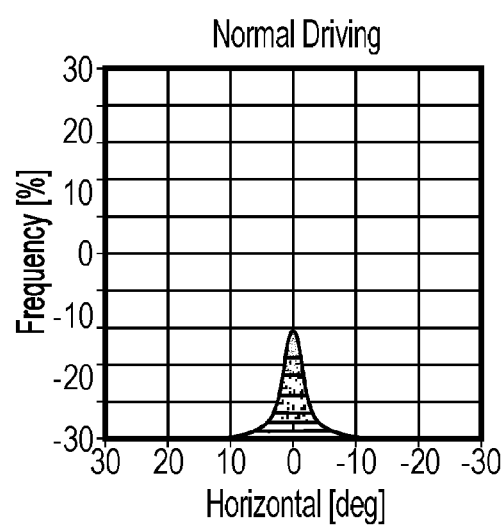
Figure 16:
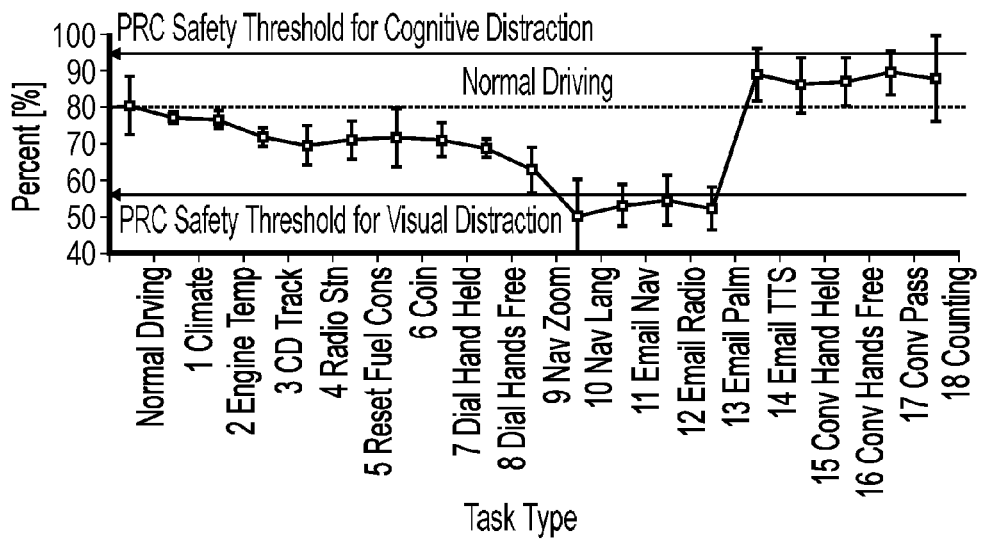
FIG. 16 is a graphical demonstration showing the use of percent road center to measure the relative impact of various in-vehicle tasks.

Many of the measures outlined herein make use of a reference calculation of the Road Center Point (RCP). The vertical and horizontal Road Center Point is calculated from a segmented eye-movement data set (segmented into fixations/smooth pursuits and saccades) of, for example, three minutes of data. First, every fixation data-point is added to a vertical and horizontal bin; for example, a bin-size of 0.98 by 0.98 degrees (128×128 for +/−30 degrees from straight ahead, or the zero point). Next, the mode of the bins (largest frequency in bin) is set as the Road Center vertical and horizontal point. These data-point-based measures are more fully described illustrated in FIGS. 12 15 where the road center point is identified based on sample density of driver eye positions. Eye movements in normal driving conditions on a straight two-lane freeway are depicted in these Figures. The data is concentrated around the road center point, and the road center point is set to zero based thereupon. The frequency in units represents the percent of total frequency per bin (one bin equals 0.98 degree by 0.98 degree). Left and upward eye movements are positive, right and downward eye movements are illustrated as being negative.

For each step in a moving time-window, for example, a one-minute time window with a 60 Hz update frequency, the following is calculated. Each fixation data-point within the time window is classified as being either of a type "1" representing a "road-center" or a type "0" representing a "non-road-center," the differentiation being made on the basis of being inside or outside the defined Road Center Area. The Road Center Area is, for example, calculated by taking the distance in degrees/radians from the Road Center Point and setting a cutoff threshold, for example, eight degrees as a radius around it. Those fixation data-points that fall within the cutoff threshold are classified as "road-center" and those that fall outside are classified as "non-road-center." In this example, the cutoff threshold defines the shape of the Road Center Area.

Figure 13:
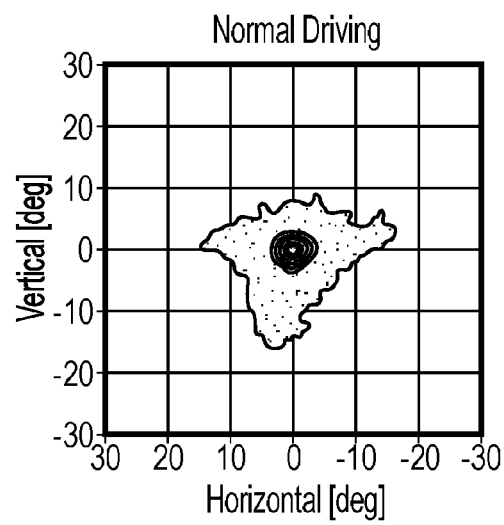
Figure 14:
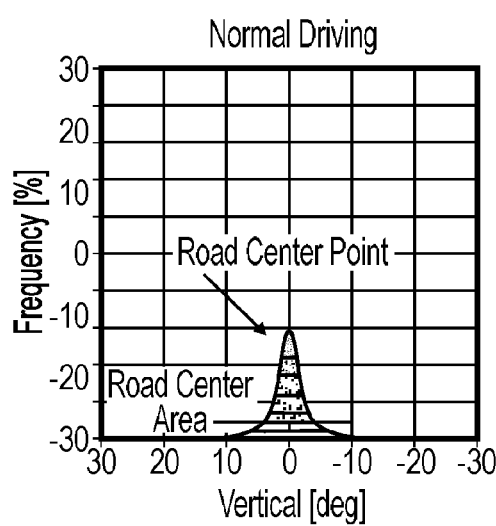

The Road Center Area can also be defined in other ways as an alternative to using a radius cutoff threshold. For example, the Road Center Area can be defined as a non-symmetrical shape. A non-symmetrical Road Center identification is useful when driving in a curved or busy road environment. Some ways to define a non-symmetrical shape are: (1) a threshold level can be set at a frequency per bin such as the horizontal Road Center Area line shown in FIG. 14. A geometric shape like the outline of FIG. 13 is the product; (2) the Road Center Area can be defined as data within, for example, one or two standard deviations from Road Center Point. Standard deviation can be defined based on the radius of the center point or separately based on the vertical and horizontal components. A vertical/horizontal standard deviation definition would enable the shape to be calculated as being oval; (3) in curved road environments, most fixation data-points are centered around the vehicle's future path. Instantaneous path trajectory is commonly calculated from vehicle yaw rate (or measures based on steering wheel angle). This curved path trajectory (converted to visual angles) can be used to define an area of valid "on-path fixations." This trajectory can be used to define an "On Path Area" of, for example, glances within a certain distance from vehicle path. Thus, PRC, A-PRC, and PLG can be calculated in the same way as described above substituting Road Center Area with On Path Area. Finally, a calculation of percentage is made by dividing the number of road-center data-points by the total number of fixation data-points within the window, and multiplying the product by 100. The percentage calculation thus ignores saccades and missing data.

Figure 17:
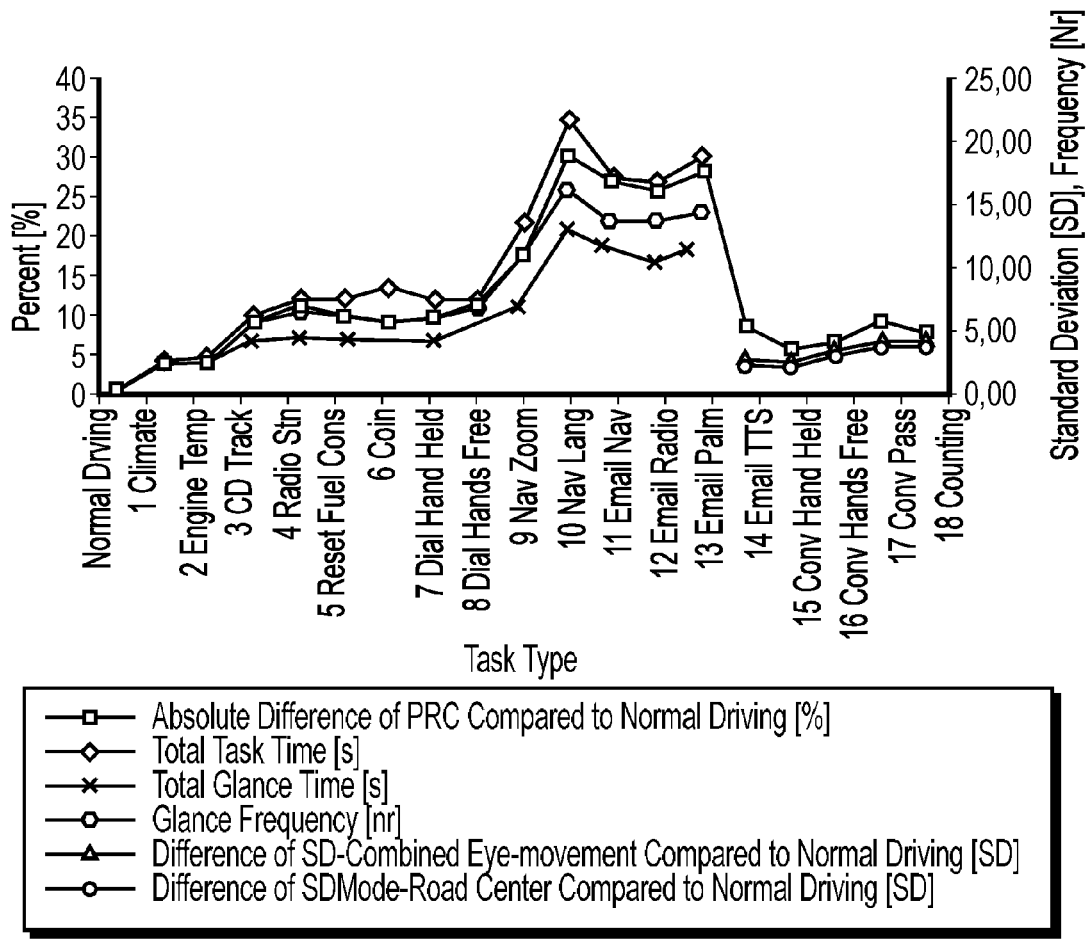
FIG. 17 is a graphical demonstration of absolute percent road center shown in relation to other measures of distraction.

Absolute Percent Road Center (A-PRC) is calculated, in the same time window as above, as the absolute difference from a given PRC value; for instance, the PRC value of normal driving. FIG. 17 shows a comparison of the A-PRC with some other common measures of distraction.

Figure 18:
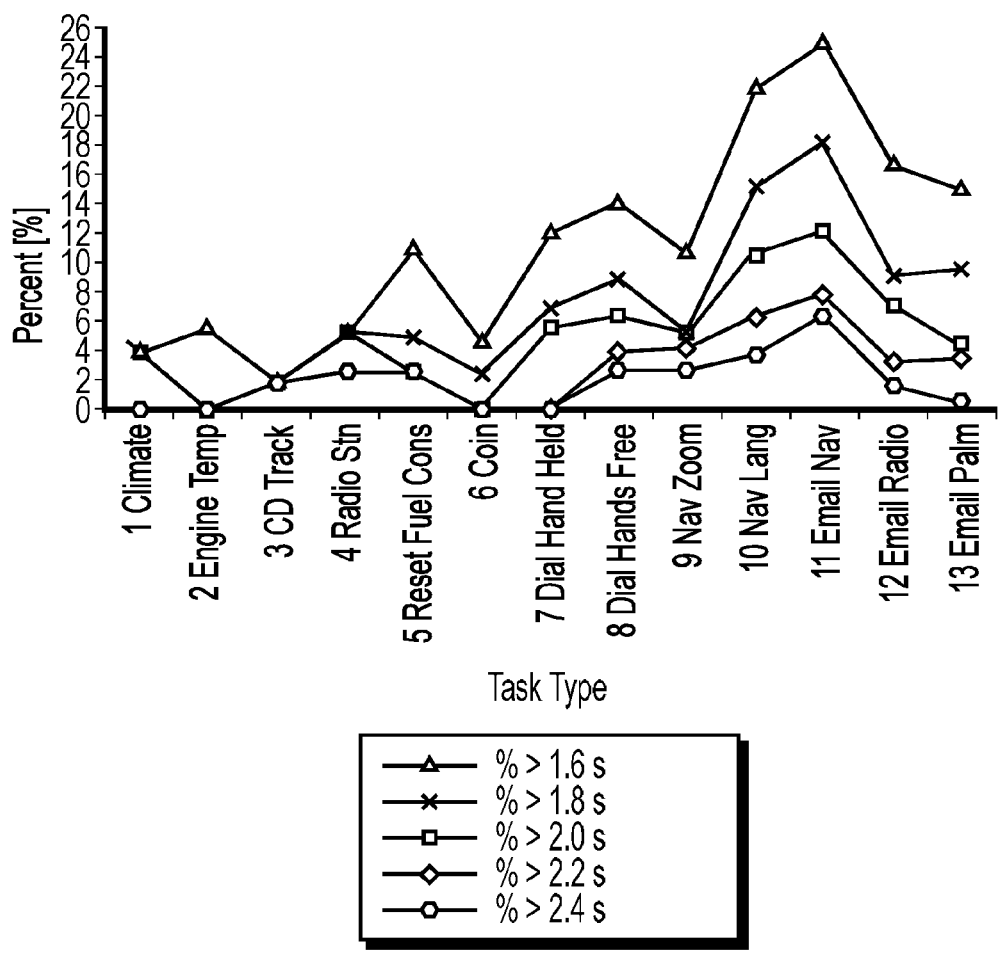
FIG. 18 is a graphical demonstration of percent long glances away from the road center for different time thresholds.

Percent Long Glances away from Road Center (PLG) is calculated, in the same time window as above, as the percent of fixation data-points which are classified as glances (as defined by the SAEJ-2396 standard) over a certain time threshold, for instance, two seconds as exemplified in FIG. 18.

Standard Deviation from Mode Road Center (SD-MRC) is calculated, in the same time window as above, according to the standard deviation formula, but with the exception that the mean is replaced with mode as exemplified by:

$$DistRoadCenter = sqrt(((VerticalPos - VerticalMode)^2) + ((Horizontal - HorizontalMode)^2))$$

$$SD\text{-}MRC = sqrt(sum((DistRoadCenter)^2)/length(Non\text{-}Fixations))$$

Percent Outside Vehicle (POV) is calculated, in the same time window as above, as the percent of fixation data-points that fall outside the vehicle and fixation data-points that fall on the rear or side mirrors. The interior of the vehicle is defined as a geometric area in degrees or radians.

An example data set was gathered relevant to the present inventions. A validation study was conducted in a simulator environment using a 7.5 m×2.2 m "powerwall" screen with one hundred and eleven degrees of view and with a resolution of 2456×750 at 48 Hz. Fourteen subjects took part in the study and various in-car tasks, such as using a mobile phone, changing radio stations and the like where preformed. The data was collected and is also available in video transcribed form according to the ISO 15007-2 method (ISO 1999). In what is referred to as the GIB-T Vigilance Study, the same simulations were performed in the environment described above and included twelve persons driving on a four-lane motorway in light traffic. Each person participated on two occasions, one drives thirty minutes under normal conditions and approximately two and one-quarter hour with sleep deprivation; the results were recorded using a video recorder. This set is part of a larger on-road experiment where sixteen subjects participated. Each person performs various in-car tasks during a thirty kilometer drive and about fifteen minutes of normal motorway driving.

Figure 19:
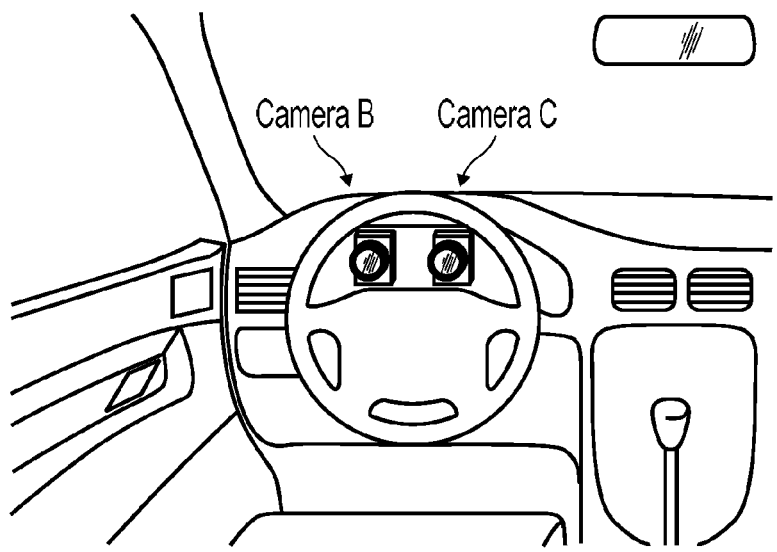
FIG. 19 is a perspective view taken inside a vehicle toward the instrument panel where two "stereo" tracking cameras or monitors reside.
Figure 20:
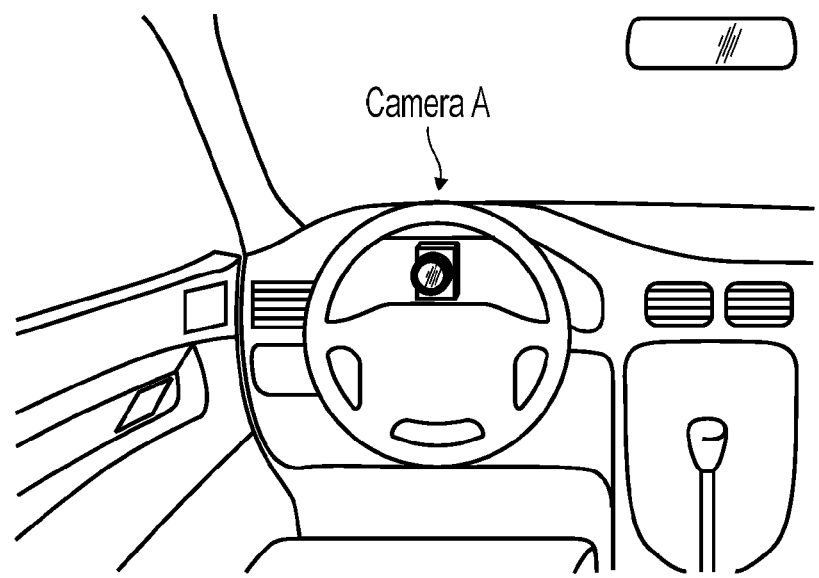
FIG. 20 is a perspective view taken inside a vehicle toward the instrument panel where a single tracking camera or monitor resides.

An exemplary tracking system tracks the head position and angle, as well as the gaze angle with respect to a fixed coordinate system. The system uses stereo-vision; that is, two cameras positioned in front of the subject driver ahead of the instrument clusters, but behind the steering wheel as depicted in FIG. 19 for tracking head position and gaze. Alternatively, and preferably, a single camera may also be utilized as illustrated in FIG. 20. This is a considerable improvement to other existing eye tracking systems that are intrusive. A tradeoff using this technique, compared to non-vision based strategies is slightly poorer gaze estimation (±3°) compared to systems that use some kind of corneal reflection (±1°). These other types of vision-based systems depend on mono-vision, and do not work as well. One substantial advantage of the presently disclosed system is that it outputs both head and eye vectors, simultaneously.

The utilized system uses a template-matching algorithm to find facial features, such as eyebrows, corner of the mouth and eyes. Each template is considered part of a 3D rigid body face model. When several features are found in both pictures, a 3D position of the head and eyes are calculated using a least-squares optimization of the model rotation and translation. The solution to this problem is biased towards points that are tracking well which make it robust with respect to occlusion, noise and perspective distortion. Furthermore, a Kalman filter is used to reduce noise and predict the head-pose in the next iteration, this reduces calculation time for the next frame.

The eye-gaze estimation is based on the head-eye position. Using a measurement of the eyeball center of rotation and the center of the iris, gaze is computed as a ray through these two points. When both eyes are visible, the gaze direction is calculated as the mean of the two vectors, otherwise the visible eye-ray is used. If none of the eyes are detectable, for example when the subject's head is turned more than some sixty degrees, or when the eyes are occluded, the face normal is used as gaze direction.

An eye-closure detection algorithm is utilized to determine whenever a subject is blinking. The distance between the upper and lower eyelids, scaled by the distance between the eye corners, is used as a measure of eye-closure. In order to compute these distances, the system uses edge detectors and then approximates parabolas, one on each eyelid, which passes through both eye corners. The eye-closure measure and a few other measures (eye-image region vertical optical flow, region temporal rate of change, nr of pixels with color of eye sclera and eye template correlation coefficient) are then weighted together and a threshold determines whenever the subject is blinking.

The system outputs a number of signals, but only a few are exemplarily described in this disclosure. These include: (1) the gaze signals "gaze_rotation_raw" and "gaze_rotation_filtered" are the same signal in the instant case since the filter parameters were set to zero in all studies. The signal consists of two directions, pitch and yaw, given in radians. (2) the "gaze_confidence" signal provides a confidence measure for the gaze estimation algorithm. (3) the "head_position_filtered" and "head_rotation_filtered" uniquely determines the 3D position and rotation of the head. These are the same as "head_position_raw" and head_rotation_raw" since all filter parameters where set to zero in the available data. (4) "tracking" status indicates whether the system is in tracking or search mode. (5) "blinking" indicates whether the subject is blinking. (6) "time" is the CPU time associated with each estimation.

It would seem that the information content in the gaze signal is not at all constant, but rather varying over time. During recordings, there are occasional glances towards objects that are unlikely to be focused at this point such as the subject driver's knees, inner ceiling of the vehicle and the like. Some of these glances can be referred to as undetected eye-closures that cause a dip in the gaze signal. The system can also be sensitive to different lighting levels. It is capable of handling changes in background lighting, however not when the change is rapid such as when the vehicle moves out from a shadowy road strip into a sunny one. The result is a high noise level and sometimes almost non-existent information content. Direct sunlight into the camera lenses makes the signal even noisier due to lens flares. Occasionally this leads to the loss of tracking for several seconds.

Figure 21:
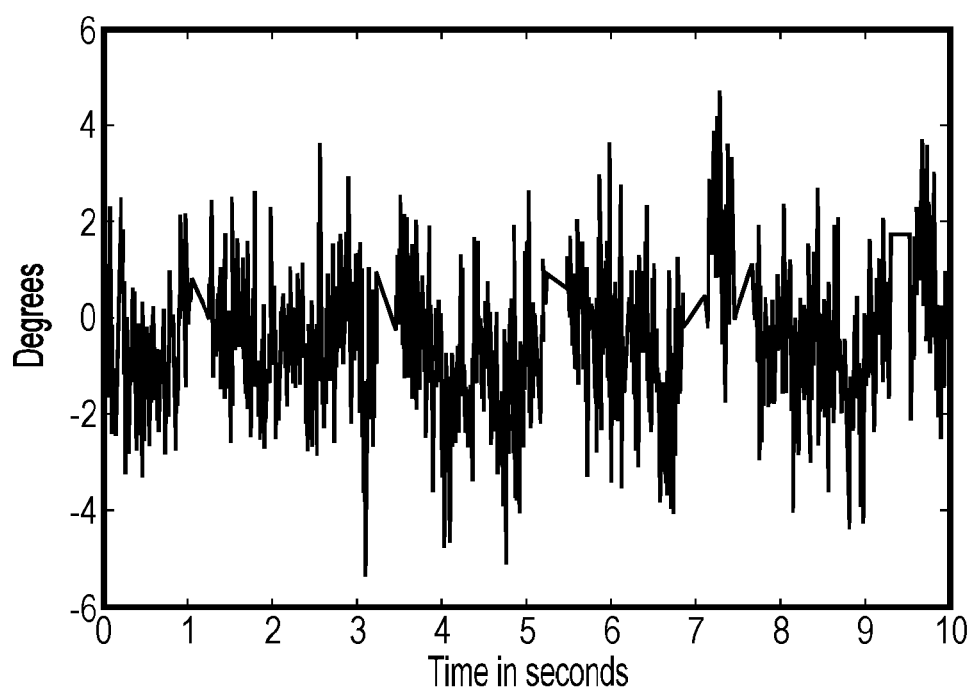
FIG. 21 is a graphical demonstration of a gaze horizontal signal with interpolated blinks.

The "dip" mentioned above during eye-closures is doubtlessly due to the fact that the eyes are closing which leads to an approximation failure (as mentioned in the introduction). The dip is very obvious in the pitch signal, some 30-40 degrees, but can also be perceived in the yaw signal. A typical blink lasts on the order of 300 milliseconds, but a dip, however, lasts only for about 100 milliseconds. Thus, the estimation does not collapse until the eyes are almost shut. The dips are easily removed in the preprocessing stage using a median filter. In an exemplary embodiment, the system simply cuts out the blinking part indicated by the blink signal and linearly interpolates between the last known sample and the first new one as is exemplified in FIG. 21 where blinks have been interpolated. The result is that significant portions of data, often almost 300 milliseconds worth, is removed and replaced with a somewhat rather unnatural representation; that is, a straight line. Since blinks often occur during saccades, no proper measurements can be made. It would be advantageous to reconstruct these features in order to make accurate measurements.

The blink signal is not always consistent with reality. This is obvious when the subject performs tasks and, according to the blink signal, never blinks but in reality it is known that blinking had to have occurred. In the exemplary system, the more a subject moves their gaze, the less accurate is the blink signal.

The gaze confidence signal could be used to overcome a large portion of the deficiencies described above. Experience, however, shows that the signal quality and gaze confidence measure does not always correlate. It can differ significantly, not only for different subjects, but also for different samples taken from the same subject. Further more, the confidence measure drops to zero with every blink. In the instance of an undetected blink, it is not possible to be certain that the incident was in fact a blink that drove confidence to zero, or an artifact. Hence, the confidence signal can not be absolutely relied upon.

The fact that the computation rate of the system is "about 60 Hz," the sampling interval is not constant but rather dependent of the computation time for each frame. In the exemplary system, however, time is available both in seconds and milliseconds, as well as a computation delay-signal in milliseconds. The delay is on the order of 150-200 milliseconds.

Finally, different subjects have different facial features making them more or less suitable for system-based measurements. Facial features with good contrast often correlate with good data quality, so does correct head position that is centered in the camera view.

The design of change detection algorithms is always a compromise between detecting true changes and avoiding false alarms. Varying noise and signal properties makes the gray zone even larger. Since the signal quality varies the idea was to use an adaptive filter to overcome this problem. Generally when an adaptive filter is proposed, it are the filtering coefficients that adapts to the signal using some kind of estimation process; for example, Least Mean Square (LMS). However, the data signals proved to have characteristics, such as changing information content and strange artifacts, which makes them less suitable for this kind of adaptation. Instead, a hybrid algorithm that makes use of two pre-processing median filters was developed. This is described in this chapter both for an off-line and a real-time algorithm. But first a brief review of some different algorithms commonly used for eye movement segmentation.

The work of Salvucci and Goldberg has been defined in "Identifying Fixations and Saccades in Eye-Tracking Protocols" wherein several different techniques have been gathered for identifying saccades and fixations.

Velocity-based
   Velocity-Threshold Identification (VT-I)
   HMM Identification (HMM-I)
Dispersion-based
   Dispersion-Threshold Identification (DT-I)
   Minimized Spanning Tree (MST) Identification (MST-I)
Area-based
   Area-of-Interest Identification (AOI-I).

Three of these were considered to be of interest for the conditions and purpose of this invention; the same being VT-I, HMM-I and DT-I. The main problem with AOI-I and MST-I are that they do not apply to the ISO/SAE standards as easily as the others.

Since verified work had already been done on the VT-I method, a first approach was made using the DT-I method. The DT-I algorithm is considered quite accurate and robust, however, the inaccuracy and noise of the eye tracker used here makes it less suitable. Saccades are identified due to noise and spikes, and fixations beginnings/endings are inaccurate due to the signal properties; for example, occasional drift before a fixation becomes more or less stationary. Another problem is smooth pursuits, which causes the algorithm to collapse when smooth pursuits are considered as one fixation. Thus, the dispersion method cannot be used alone.

The HMM-I, on the other hand, makes use of probabilistic analysis to determine the most likely identification. The HMM model in HMM-I is a two state model. The first state represents higher velocity saccade points; the second state represents lower velocity fixation points. Given its transition probabilities, the HMM-I determines the most likely identification of each protocol point by means of maximizing probabilities. The algorithm is considered to be accurate and robust, given the right parameters. These are estimated using a re-estimation process, the primary intricacy of HMMs. The implementation of this estimation is both complex and tedious.

The VT-I algorithm does not have the problems mentioned above. However, the velocity threshold is a compromise between picking up noise and identifying accurate fixation beginning and ending. In order to minimize this problem, a dual-threshold algorithm was adopted (DualVT-I). A high threshold ensures proper saccade identification. If a saccade is detected, the low threshold is used to calculate the beginning and end.

The primary disadvantage of the VT-I algorithm was the lack of robustness. This is however greatly improved in the DualVT-I.

None of the identification methods described in the previous section are in any way perfect; they all have different flaws. Hence, a combination of two algorithms and the additional rules for eye movements where chosen for this work, namely the DualVT-I and DT-I. This combination works as an adaptive algorithm in the sense that the decision-making is automatically biased towards the DT-I and rule-based part while preserving the DualVT-I properties as noise increases. This combines the exactness of the DualVT-I velocity protocol and the robustness of the DT-I dispersion protocol. One way to look at it is to consider the rules as algorithm control, meaning they bias the "decision" towards the algorithm part working most accurately at the present time. The algorithm cooperation is illustrated in FIG. 4.

Regarding preprocessing, the raw-data needs to be preprocessed prior to segmentation. It is more or less noisy and contains blinks and non-tracking parts.

Figure 22:
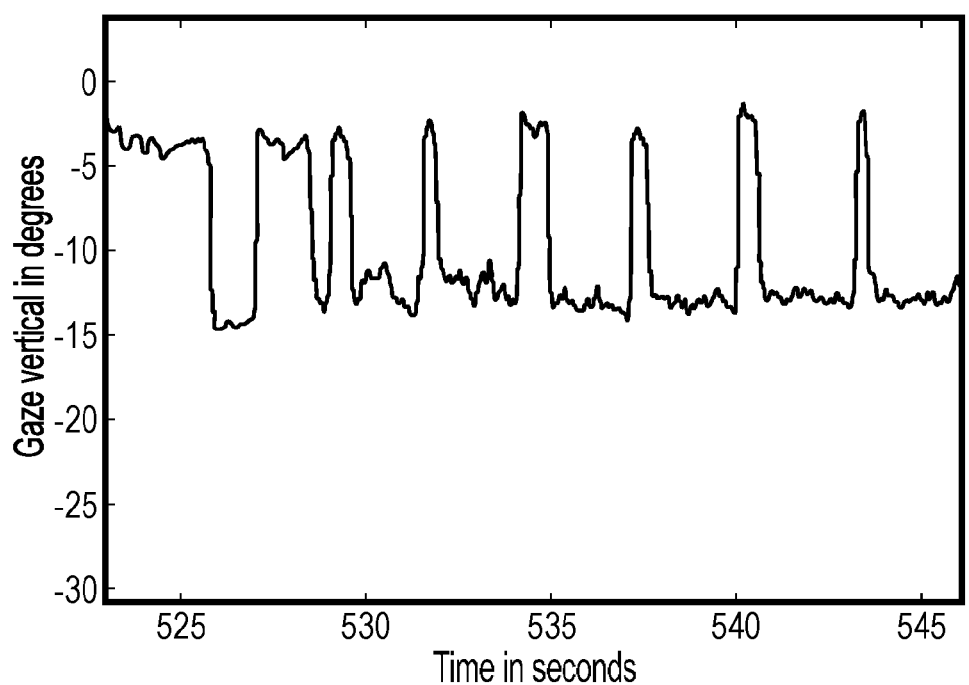
FIG. 22 is a graphical demonstration of horizontal gazes and showing three dips due to blinking.

Many researchers have pointed out median filters and FIR-hybrid-median (FHM) filters to be appropriate for eye movements. The median filters special characteristics to preserve sharp edges while noise and outliers are subdued is suitable for saccadic signals. In general FHM or a weighted-FHM filter is considered to work best, however a 15 sample sliding-window median filter reduces noise sufficiently. As a positive side effect it also suppresses the "blink dips", produced whenever the subject blinks, enough to pass the segmentation undetected as demonstrated in FIG. 22.

A completely different problem is the blink interpolation as described earlier and in which the gaze signal is replaced by a linear interpolation. If this occurs during a fixation, it is usually no problem. However, humans often blink during saccades that only last for some 100 ms while 200-300 ms are replaced with a straight line. To get around this problem a reconstruction is necessary. The present invention employs a simple, robust solution that provides a proper number of glances, whereas time based measures are less accurate. Noise, of the same amplitude as present in the signal, is added to all blinks with dispersion less than five degrees and all other blinks are marked as saccades. The five-degree threshold was set based on all the data available, without detecting any false fixations. Fortunately, subjects tend to blink less during tasks with multiple glances.

As mentioned earlier, the identification algorithm chosen is a hybrid between the velocity and dispersion protocol as well as rules outlined by the physical properties of the eyes and eye tracker equipment. In the off-line version, the processes run in series, at first the velocity protocol using a dual threshold is applied and then the dispersion protocol with the rules. This is illustrated in FIG. 1. A fixation restoration algorithm is used when noise or some other property of the signal has prevented the detection of a fixation (that should be there according to the ocular rules). This is illustrated as an arrow back from the DT-I and rule-based block to the DualVT-I block. Also, the automatic clustering algorithm has been included into the hybrid shell. It administers the glance detection.

Each algorithm part will now be further described. The derivative (velocity) estimate is computed by means of a two-point central difference:

$$\partial y(x) = \frac{y(x+h) - y(x-h)}{2h}$$

applied to each gaze component and then weighted together with a square-sum-root to form the 2-D velocity. Noise is always a problem when differentiating a signal, one way to handle this problem is to low-pass filter the derivatives. The central difference however, can be described as an ideal differentiator and a low-pass filter in series. The frequency response is calculated:

$$\dot{Y}(\omega T) = \frac{Y(\omega T) j \sin(\omega T)}{T}$$

Figure 23:
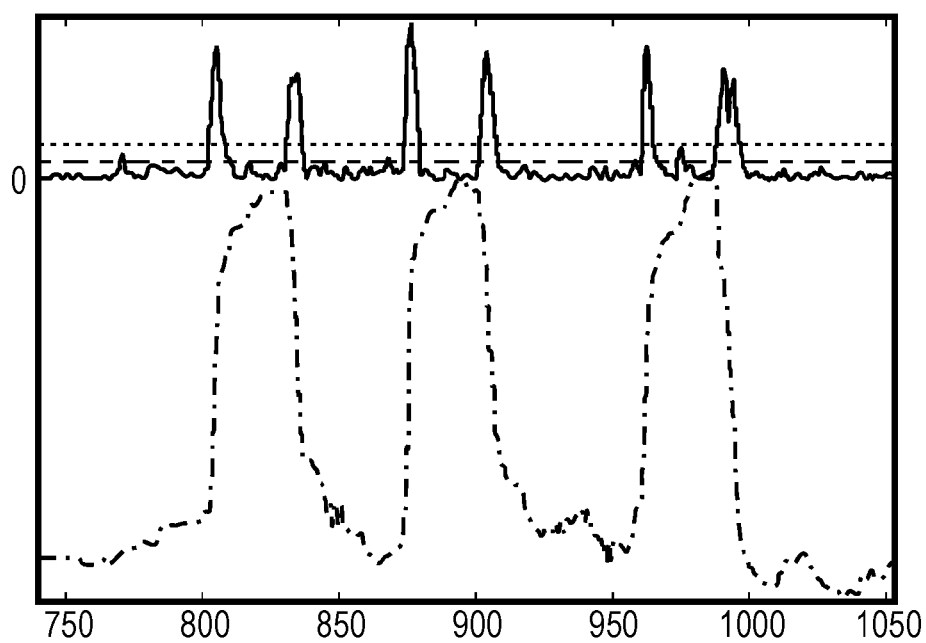
FIG. 23 is a graphical demonstration on eye motion velocity with respect to thresholds.

With the sampling rate set to approximately 60 Hz, this filter has a 3 dB cut off frequency of about 14 Hz. This rather low cut-off prevents aliasing, ensuring that frequencies of more than 30 Hz are subdued but still high enough not to distort saccade beginnings and endings. The dual thresholds and the velocity estimate are shown in FIG. 23.

One experimental comparison of five derivative algorithms found the two-point central difference to be the most accurate technique for 12-bit data. Among the advantages of this method are that it is simple, accurate and fast.

Thresholds for the saccade detection where set primarily by comparing the results with the results of previously performed semi-automated analysis.

Now, although the derivative approximation is automatically low-pass filtered it is still very noisy, the noise level being at approximately 70°/s. However, since the data gathering system has an inaccuracy of ±3° at the best, and the peak velocity of saccadic movement is higher than 100°/s for amplitudes larger than some three-four degrees, no problem is posed. Despite this, practical evaluations have shown that the occasional error may slip through, especially when noise increases. Those inaccurate identifications are detected and removed by the DT-I part in the next step of the segmentation process. Thus the accuracy tradeoff using three samples for the velocity estimation has proved to be negligible.

Figure 24:
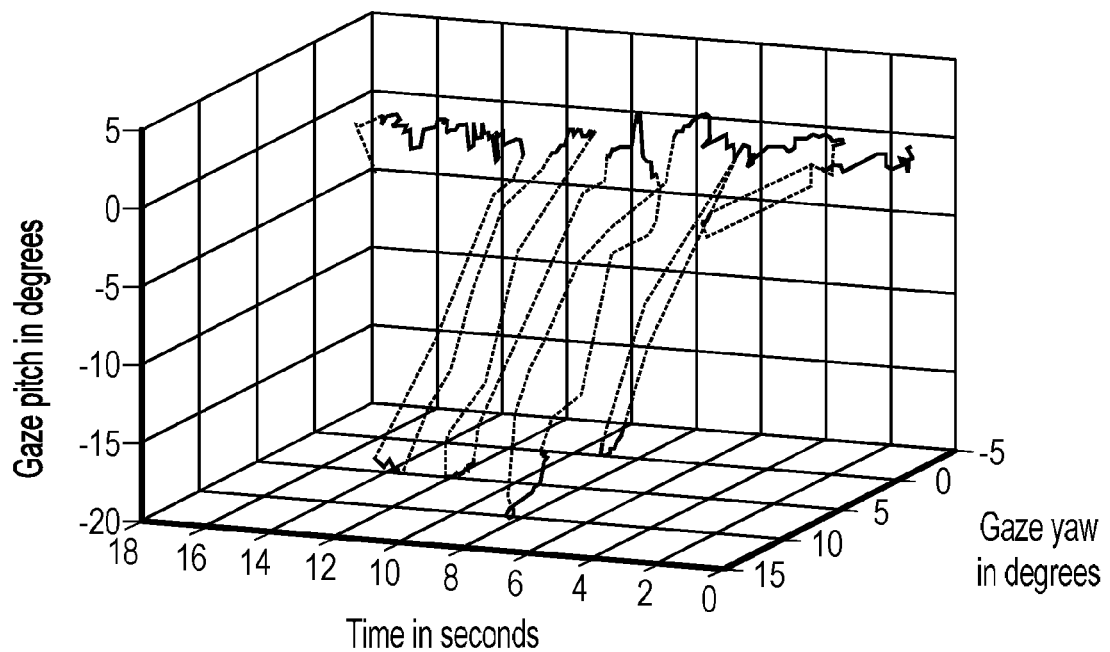
FIG. 24 is a graphical demonstration of a segmented gaze signal.

In the second step, the physical criteria stated hereinabove, and parts of the dispersion-based algorithm determine if detected saccades and fixation are valid (rules application). A three-dimensional representation of exemplary saccades and fixations is provided in FIG. 24. When the noise level is high, the derivative approximation becomes more sensitive and confusing artifacts are occasionally detected within fixations. Their removal has a few ground rules preventing misjudgment: 1) A saccade can be altered into part of a fixation if the new fixation dispersion is less than a threshold; and 2) A saccade can be altered into part of a fixation if the variance of the fixations is less than a threshold.

If these criteria are fulfilled, the two fixations are joined using a linear interpolation with some added noise. The noise is introduced in order to avoid making this part of the signal non-physical. The original signal often contains a spike of some sort, hence the interpolation.

Likewise, fixations are removed and simply marked as saccades if they are non-physical, meaning the duration is less than some 150 ms. This occurs when the signal's information content is low.

Figure 25:
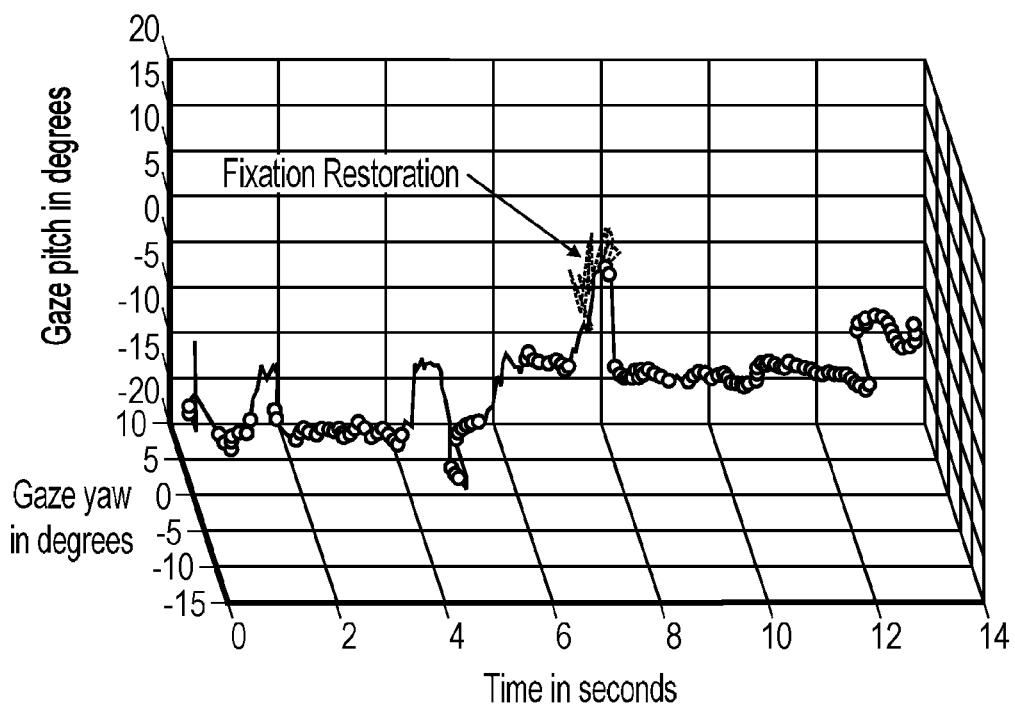
FIG. 25 is a graphical demonstration of a restored fixation.

In the offline version (when a long delay is acceptable), a fixation restoration algorithm as illustrated in FIG. 25 has been developed to compensate for the, sometimes, low information content in the gaze signal. This can occur in the beginning of a fixation when the algorithms have not stabilized themselves. It works under the assumption that a saccade is not likely to last longer than some 200 ms and if that is the case, it is most probably two saccades and an undetected fixation in between. Based on this the algorithm locates saccades that might contain an undetected fixation and then filter them using a sliding median filter somewhat longer than the one used in the preprocessing (20 samples). This calms the signal noise enough to, sometimes, detect a new fixation. Now, this may seem as a straightforward and dangerous method, more or less forcing detection. It is, however, merely an adaptive property of the segmentation formula and has been proved to correlate strongly with reality with respect to the validation portion.

The glance classification algorithm works in two steps. At first, all clusters are automatically localized based on their total dwell-time. In the second step these clusters are clustered themselves, based on the same dwell data, and world model objects are formed. A world model is a simple description of different pre-defined view areas, for example, the right rear view mirror or the road strait ahead. All models are defined in a plan perpendicular to the driver when he/she looks at the road straight ahead.

Figure 26:
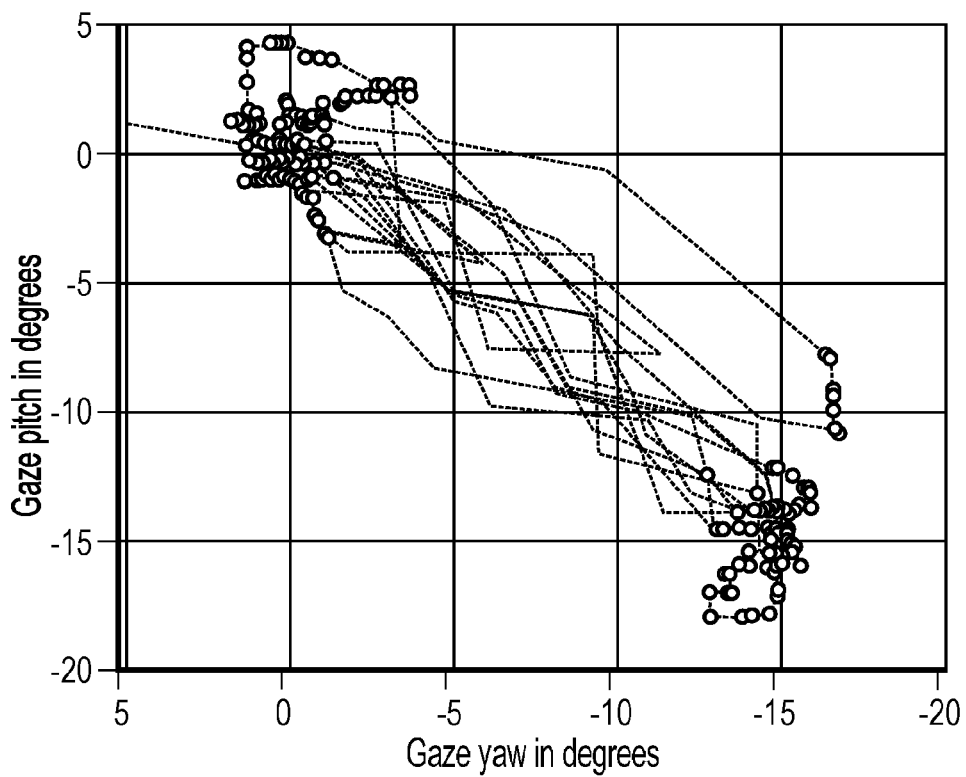
FIG. 26 is a graphical demonstration of multiple glances away from the road-ahead-scene.
Figure 27:
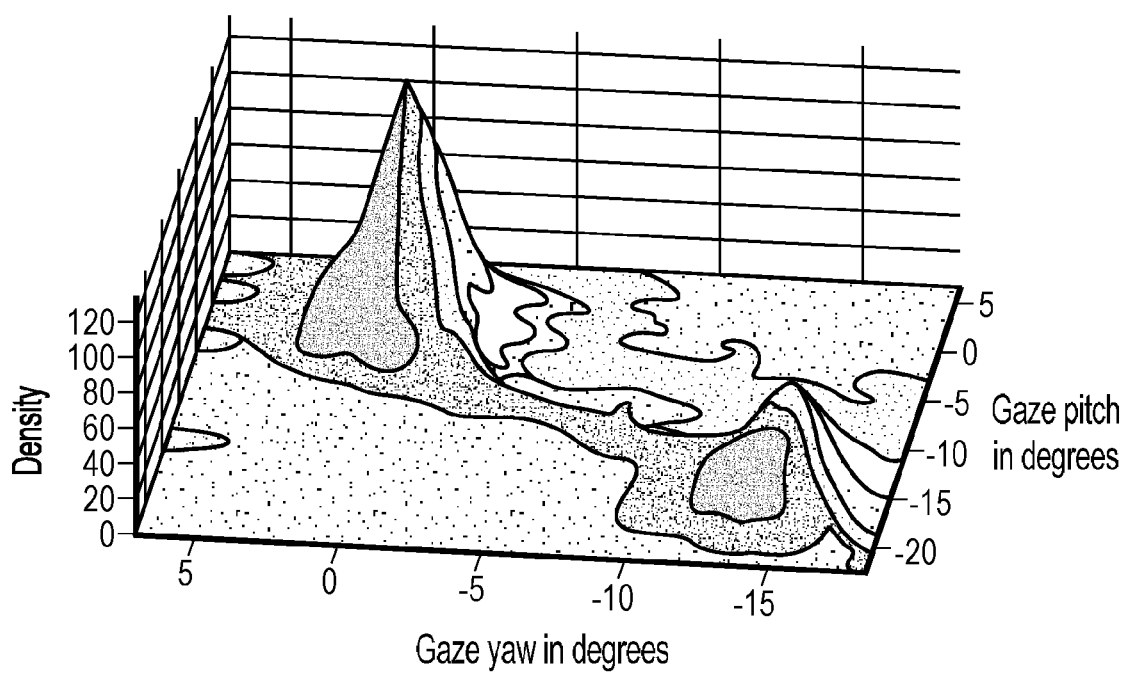
FIG. 27 is a dwell histogram showing two areas/objects of interest.

In the first step, a rough approximation of cluster locations is done using a 2D dwell-time-histogram; that is, total fixation time in different view areas based on the duration and mean position of each fixation as depicted in FIGS. 26 and 27. Usage of the mean position has proved to be a simple way to reduce noise problems. The histogram bin-size was set to 3-by-3 degrees, mainly by trial an error. This creates a nice, smooth histogram where every peak indicates the approximate position of a cluster. Since gaze data is given in radians, the actual cluster plane is not a plane, but rather the inside of a cylinder. Thus, the gaze angle does not affect the cluster size. Once the approximate cluster positions are determined, every mean fixation-point is assigned to the nearest cluster-point, by Euclidian means. All clusters are then updated to the mean position of the points associated to respective cluster.

The algorithm also creates a classification log where every classified event is stored in a matrix with its position, beginning, termination, duration, associated cluster and type encoded into numbers where the type is saccade or fixation. The log-matrix is simply a data reduction and, later on, used as base for statistical function calculations.

In the second step, all clusters are mapped onto a world model. Different geometric areas, for example boxes, circles or combinations of the same or other shapes, define objects such as mirrors, center stack, instrument clusters, and the like. Several clusters are usually within the same area belonging to the same glance. These are now joined to one cluster and its mean position recalculated. The number of world model objects varies with the task. A base model of three objects has been chosen for this work and an algorithm based on the dwell histogram makes the objects "float" into place. It then calculates the standard deviation of the distance between the objects center and all cluster positions. The clusters that fall within the 95% confidence values of an object are considered to be a part of it, thus the object size is adjusted to enclose the cluster. The number of world model objects is easily controlled via a parameter.

This is one step that can require inspection and, sometimes, correction from the experimenter. This is because decisions on what is and what is not an object are very difficult due to noise and non-tracking in the raw signal; qualified guesses have to be made by the experimenter. One way to eliminate the need for human rating is to avoid sunny days when collecting data. Direct sunlight into the cameras is the one cause that stands for almost all fixation dislocations.

The world model approach could be very useful for other measurement purposes besides glance classification; e.g., on-road off-road ratio and larger scale visual scan-patterns. It is also useful when the gaze signal is noisy or corrupt (e.g. by sunlight) and fixations are scattered in larger areas forming more clusters than there really are. During the process, the log-matrix is updated continuously.

When templating areas of interest, there are two primary problems: 1) it needs to be calibrated for each and every subject, and run; and 2) the objects often need to be defined larger than they really are due to the inaccuracy of the sensor system. It is difficult to determine how large a world object needs to be before examining the data. If the object is too large there is always a possibility that outliers are included or that objects has to overlap each other.

In light of this, it is easier to define the world model when analyzing the data and let it adapt to the current situation.

At last, the statistical measures are produced using a log-matrix. The measures are as defined as: 1) dwell time; 2) Glance duration; 3) Glance frequency; 4) Total glance time; 5) Glance probability; 6) Link value probability; 7) Time off road scene ahead; 8) Total task time; and 9) Transition time.

Once the glance classification is performed, the calculation of these measures are straightforward, and are therefore not included.

An exemplary real time implementation is very much like the off line algorithm. The differences are that only "road-scene-ahead" and "other-areas" are defined as world model objects. The output is, for each task, total number of glances and total glance-time on and off road. Task beginning and ending are indicated in the log-file by annotations or time-gaps (this is done manually during logging).

Before any classification is performed, the road-scene-ahead world object is localized. This is done using an initialization phase, calibrating the setup for the particular subject and run. The road-scene-ahead area is localized by means of a gaze density function. Most of the driver attention is directed in this area and the dwell time density function always have a very significant peak in the center of it as shown in FIG. 27. The distribution of fixations in this area is approximated to be Gaussian. Thus, the standard deviation can be computed using the highest point in the dwell histogram as the average fixation position value. Technically, it is not the standard deviation being calculated, but rather deviation of mode. The road-scene-ahead is then considered to be within the 95% confidence values. The procedure is done for both yaw and pitch respectively, thus forming an oval area that represents the road-scene-ahead.

Figure 29:
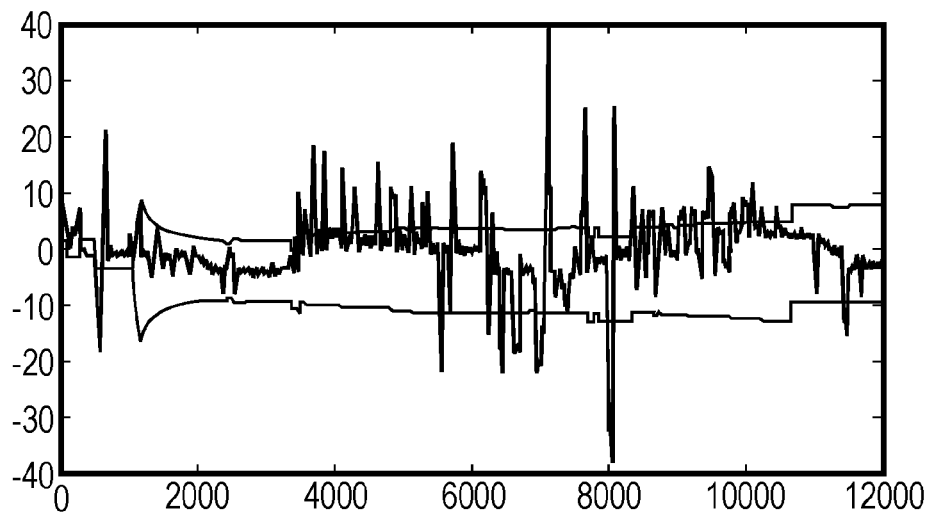
FIG. 29 graphically demonstrates the establishment of road-scene-ahead boundaries.
Figure 30:
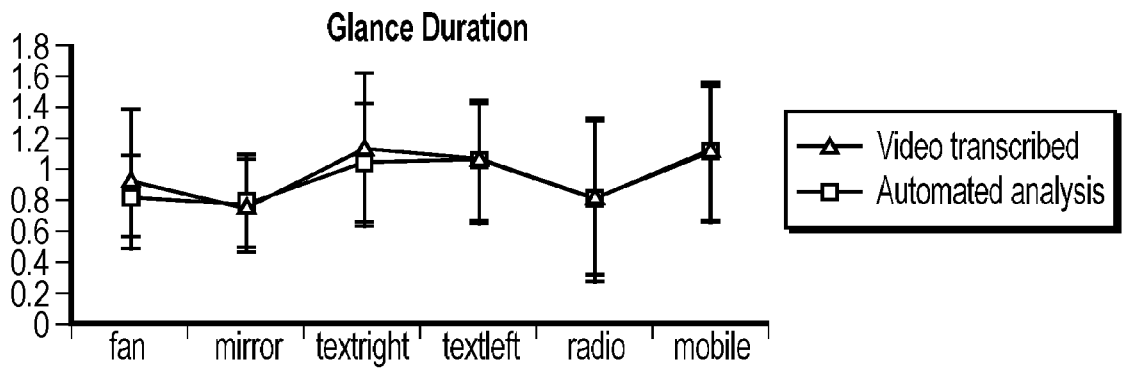
FIGS. 30-33 are graphical demonstrations of various components are aspects of typical glances made by a driver.
Figure 31:
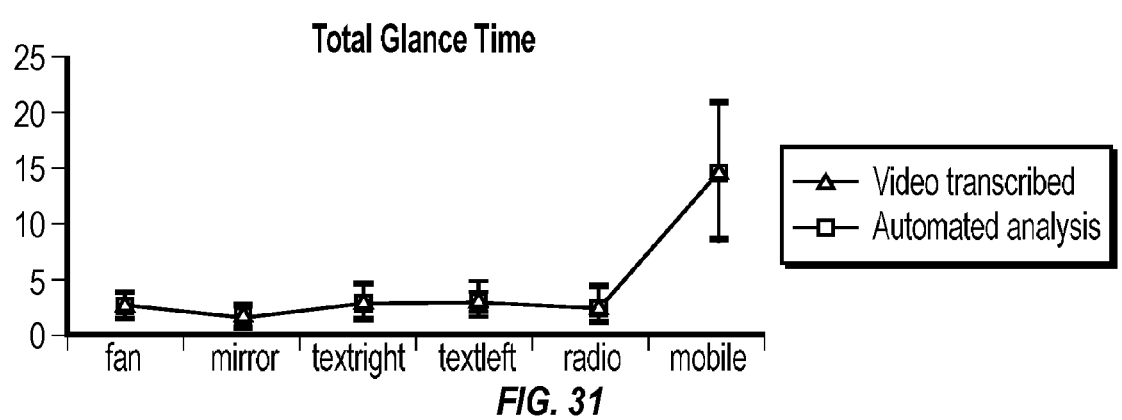
Figure 32:
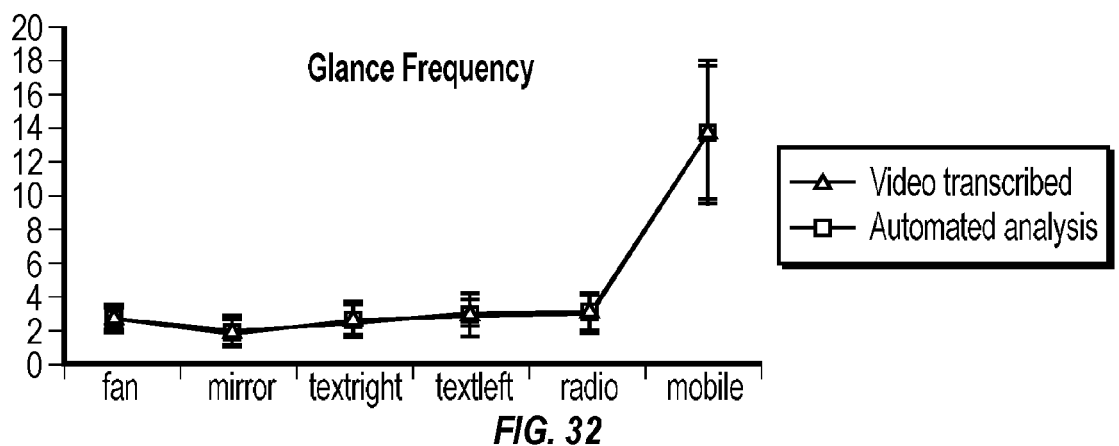
Figure 33:
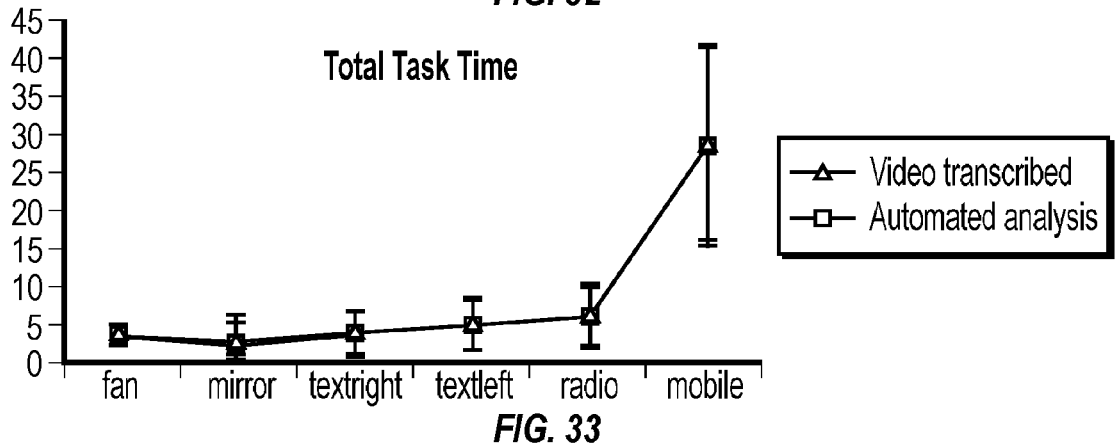

During the initialization the search area is limited to what probably is the road-scene-ahead; typically a circle with radius 10° and center in (0,0) and only fixations falling into this area are used for calculations. Despite this, the 95% confidence boundaries had to be biased about 2 degrees down and to the right in order to make it work with some subjects; a characteristic that arises when a subject's gaze follows the road curvature. Simple solutions to these deviations are exemplarily longer initialization periods or an additional calculation, using a time window that allows it to follow the curvature. If yaw-rate was available, the center of road-scene-ahead could probably adapt to this signal and solve the problem, however this is not a common sensor in vehicles at the present time. The initialization phase can be seen in FIG. 29. The calibration process was tuned to work at an optimum using approximately five minutes of normal driving before producing valid values.

A similar problem arises when the driver is performing a task. The eyes do not seem to return to the center of the road-ahead area, but rather a few degrees in the direction of the secondary task (driving being the primary). Head bias could be the answer to this behavior meaning it is not perpendicular to the road-scene-ahead thus introducing a bias in the gaze estimate. The more the subject looks away from what is the road-scene-ahead the less accurate is the gaze estimate.

As soon as the initialization phase is finished, the DualVT-I, DT-I and rules are enabled. The DualVT-I first identifies saccade-fixation combinations. This, the shortest form of a glance, is then forwarded to the DT-I and rules along with its glance time. Mini glances, for instance a sequence of fixations within an area are joined if they belong to the same area; that is, glances according to the ISO/SAE standards are formed. Glance times are summed and forwarded to a counter synchronized with an on/off-road-ahead signal, which is the output from the clustering algorithm as depicted in FIG. 28. The counter registers all glances and glance-times belonging to the same task and is then reset for every new task. Before the reset is performed, however, the data is sent processed for logging purposes. In this case, time-gaps have been used to indicate the beginning and ending of tasks.

The algorithms have been validated to data from the VDM validation study utilizing video transcription. The video transcription was conducted according to the ISO 15007-2 and the SAEJ-2396 method. Using seven subjects, four measures where compared: 1) task length; 2) glance frequency; 3) average glance duration; and 4) Total glance time.

The validation was preformed task-by-task with every glance visually confirmed to ensure proper algorithm function. A few fixations were automatically restored using the restoration algorithm that proved to work very well and actually did no miscalculations.

Pearson product-movement revealed high correlations between analysis types on all important measures: task length $r=0.999$, glance frequency $r=0.998$, average glance duration $r=0.816$ and total glance duration $r=0.995$. This is to be compared with the results in "Automating Driver Visual Behavior Measurement" where the correlations where $r=0.991$, $r=0.997$, $r=0.732$ and $r=0.995$ respectively. FIGS. 30-33 plot the mean and standard deviations for each task.

The real-time algorithm has been validated against six video transcribed subjects from the VDM validation study. One of the subjects used in the offline validation had to be left out due to the absence of a baseline drive (no calibration data).

Three measures where compared: 1) Number of glances; 2) Total glance time; and 3) Average glance time.

Figure 34:
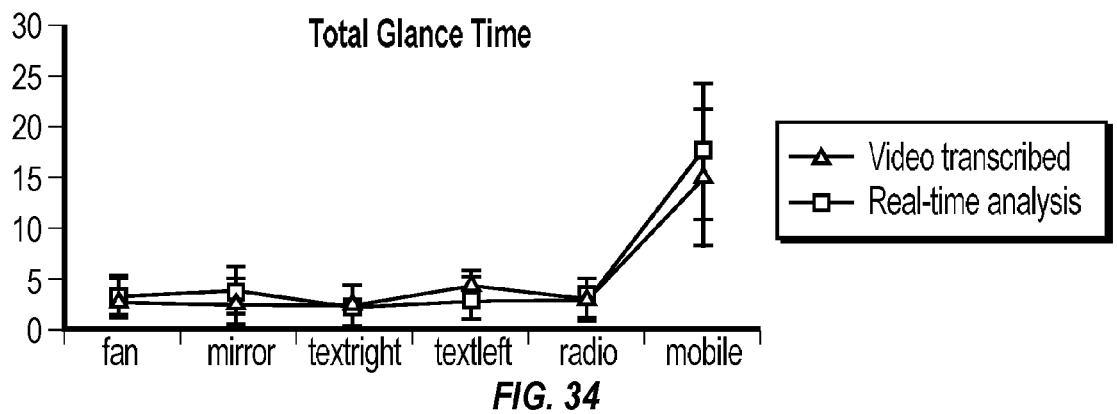
FIGS. 34-36 are graphical demonstrations of certain statistical analysis of glance data.
Figure 35:
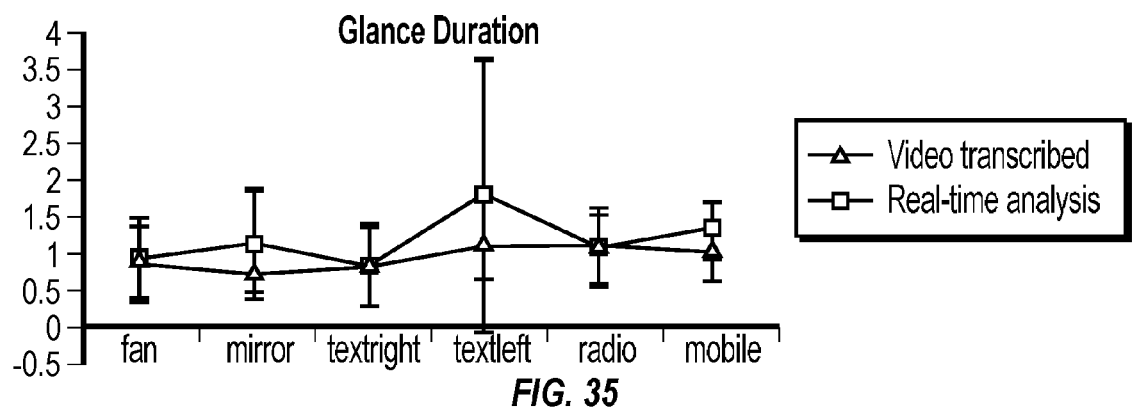
Figure 36:
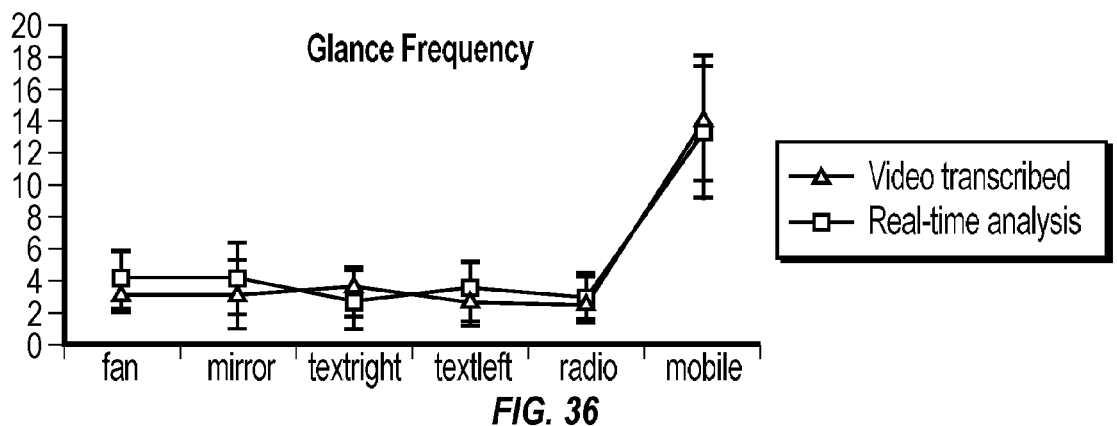

The entire drive of each subject was run in series through the algorithm. To be on the safe side every run started with 20 minutes of normal motorway (baseline) driving to calibrate the system although only five minutes are required. Pearson product-movement revealed high correlations between analysis type on two measures: Number of glances, $r=0.925$, and Total glance time, r=0.964. Average glance time, however, did not correlate very well, r=0.301. FIGS. 34-36 plot the means and standard deviations for each task.

The results from the validation prove that the algorithms are outstandingly reliable, even when data quality is not at its optimum level; for example, the algorithms are robust to varying noise level and signal accuracy. Also, using ocular motion rules, the algorithm can retrieve fixations that have almost vanished in the signal.

The correlation between analysis methods is very high, in the region of 0.99 (off-line version) for all measures except average glance duration, which is still strong (r=0.82). A low correlation could however be expected from a measure based on two others.

The preprocessing also proved to worked well. The 15-sample median filter preserved saccade beginnings/terminations while subduing noise and blinks very efficiently.

The combination of the DualVT-I, the DT-I and the rules proved to work beyond expectations. The accuracy of the DualVT-I and the reliability of the DT-I in collaboration with the physical rules for eye movements formed an algorithm that is robust to temporary sensor confidence drops and high noise levels.

It has been shown that it is possible to have robust and reliable real-time glance detection. The simulation reveled high correlations on two measures (number of glances and total glance time). The correlation for average glance time was, however, low (r=0.301). Keeping in mind that the real time algorithm cannot differ a glance towards the mirror from one to the radio, all measures could be expected to be rather low. It is it is possible to make the real-time algorithm as accurate as the off-line version. This will be achieved by identifying the objects most commonly looked at inside the vehicle; for example, the interior mirror, side mirrors, instrument cluster and center stack. These objects are fairly spread out in the vehicle and therefore will not be confused with each other. Moreover, it should take only one or two glances in the area that is defined as the most probable area for one of those objects to start an initiation phase for this particular object. The objects most commonly looked at are the ones contributing the most to this error and these are also the ones that are the easiest to detect.

Since no other data set is video transcribed or in any other way analyzed, it has only been used for testing different algorithm parts e.g. the real-time initialization. However, this work has opened the door for the analysis of this data.

A robust hybrid algorithm that works according to the definitions and measures in the ISO 15007-2 and SAEJ-2396 standards has been developed. The method is substantially faster than video transcription, one hour of data takes about one day to video transcribe compared to a few minutes with the algorithms which also automatically adapts to the present noise level.

During the course of the development of the present invention(s), the following achievements have been observed: 1) The preprocessing median filtering length is optimized to 15 samples for data sampled at 60 Hz; 2) A median filter with 20 samples is used on noisy signal parts where, according to the ocular rules, there should be a fixation. This calms the signal enough to detect the fixation; 3) A robust hybrid of two fixation/saccade detection algorithms, which adapts to the present noise level, and the decision algorithm has been developed and tuned for 60 Hz data; 4) Physical rules for eye movements are implemented as a smart decision-making and controlling algorithm; 5) An automatic and robust clustering method that requires a minimum of interaction has been developed for task analysis; 6) A real-time version of the algorithm has been developed and validated; 7) The real-time version of the algorithm uses a novel framework which segments glances into the "road-straight-ahead" or "other" categories; and 8) All measures in the ISO/SAE have been implemented.

This thesis opens doors for several interesting in-vehicle product applications which could make use of eye movement data to be tested in a real on-road environment. For example: workload estimation, attention estimation, drowsiness detection, adaptive interfaces, adaptive warnings etc. Ergonomic evaluations, HMI studies, studies of cognitive workload, distraction, drowsiness and the like are all potentially interesting applications of the inventions defined therein.

Thus, a new path into the drivers mind has been opened. In today's environment, there still are a few manual steps to carry out such as load and save data, visually inspect the segmentation and occasionally adjust the world model. It is contemplated, however, and well within the understanding of those persons skilled in the relevant art to automate these manual tasks and execute the same according to the present invention. This is especially the case with direct sunlight into the cameras that scatters fixations over large areas that sometimes even "melts" clusters together. Thus, that analysis tools become more robust and accurate, some of these steps will no longer be necessary and perhaps batch processing will be possible.

The invention contemplates having a real-time algorithm that works robustly and intelligently to provide vehicles (and researchers) with as much usable information as possible from the driver's eyes. The real-time algorithm will be able to classify several objects robustly and intelligently. The real-time adaptation of world model objects to the real world will log events and data. One interesting approach is to implement target areas as HMM states. Introducing this statistical approach target classification may be enhanced, as it would make the target area boundaries more floating. One interesting idea is to have world model areas pop up when ever fixations are registered outside or at a distance away from the other objects, a dynamic world model. The world model could use this history of objects to calibrate the world model and make intelligent decisions; for example, an entirely task driven identification of objects.

Regarding the detection algorithms, other sensor information can be utilized. In modern cars the CAN bus is full of sensor signals that might be useful to estimate gaze direction when tracking fails such as steering angle, turn indicator actuation, vehicle speed, and whether or not certain buttons are pressed. This could also provide information about the traffic environment and thus optimize segmentation parameters for specific traffic environments such as country, suburban and city traffic. A rather successful approach to recognizing large scale driving patterns has also been completed.

Other WHM-filters can be tested for finding out if there is a better way to reduce noise in the beginning of fixations away from the road where the restoration algorithm is used. The flora of filters seems to be enormous.

One way to support the algorithm could be the fact that a subject's head often moves in the same direction as the eyes, at least for lateral gaze. A drawback with this approach results from individual differences in subjects. Some subjects virtually do not move their head at all while some always do. Still, this might be a suitable way to aid the segmentation when gaze is noisy.

In the real-time algorithm, a prediction of the next six samples would increase speed with 100 ms. It has been shown that saccadic signals can be predicted, at least a few points, with very small errors using a five point quadratic predictor. Speed is of the highest importance in a real-time algorithm.

In light of what is mentioned above, it is clear that the fine tuning of these algorithms will continue in the future. One development that is already underway is an algorithm GUI, called "Visual Demand Measurement Tool" or simply "VDM-Tool" The purpose of this program is to make the analysis tools easy to use for anyone who whishes to analyze eye-movements.

Many aspects of the inventive analysis techniques, including both the methods and the arrangements upon which those methods may be executed, are disclosed. Important characteristics of the analysis include at least a partial basis on driver eye movements, and assessments being made on a real-time basis.

The invention claimed is:

1. A method for hierarchically analyzing ocular then head orientation characteristics of a driver of a vehicle in order to identify locations of driver interest while driving the vehicle, said method comprising:
    detecting, utilizing an optical sensor, and quantifying a position and orientation of a presently driving driver's head relative to an interior space within a passenger compartment of a vehicle and also simultaneously detecting, when visible to the sensor, driver ocular orientation;
    providing a reference-base position of a reference driver's head relative to the interior space within the passenger compartment of the vehicle together with probable locations of driver interest correlated to different (1) ocular orientations and (2) head orientations relative the reference-base position of the reference driver's head; and
    normalizing said quantification of the position of the driver's head to said reference-base position and hierarchically comparing the quantified (1) driver ocular orientation when available, or the quantified (2) driver head orientation if quantified driver ocular orientation is not available, against the correlated probable locations of driver interest relative the reference driver's head and thereby enabling deducement of a corresponding probable location of driver interest based on the quantified orientation of either (1) the driver's ocular orientation or (2) the driver head orientation.

2. The method as recited in claim 1, further comprising:
    preferentially utilizing detected information regarding driver ocular orientation as basis for said deducement of location(s) of driver interest; and
    switching to utilization of detected information regarding driver head orientation as basis for said deducement of location(s) of driver interest when the quality of said detected information regarding driver ocular orientation degrades beyond a prescribed threshold gaze confidence level.

3. The method as recited in claim 2, wherein said threshold gaze confidence level is exceeded when the driver's eyes are occluded.

4. The method as recited in claim 2, wherein said threshold gaze confidence level is exceeded when the driver's head orientation departs away from an eyes-forward orientation beyond an allowed degree of deviation.

5. The method as recited in claim 1, further comprising:
    utilizing a mathematic transformation for accomplishing said normalization of said quantification of the position of the driver's head to said reference-base position.

6. The method as recited in claim 5, further comprising:
    performing said mathematic transformation using a vehicle-based computer on a substantially real time basis.

7. The method as recited in claim 1, further comprising:
    defining probable locations of driver interest relative to said reference-base position based on detected head orientation.

8. The method as recited in claim 1, further comprising:
    defining probable locations of driver interest relative to said reference-base position based on detected driver ocular characteristics.

9. The method as recited in claim 8, further comprising:
    establishing said definitions of probable locations of driver interest relative to said reference-base position based on the detected driver ocular characteristic of gaze frequency.

10. The method as recited in claim 9, further comprising:
    quantifying said establishment of said gaze frequency based on collected gaze density characteristics.

11. The method as recited in claim 9 further comprising:
    identifying a probable location of driver interest based on driver ocular characteristics by mapping detected driver ocular orientation to one of said prescribed or defined probable locations of probable driver interest relative to said reference-base position.

12. The method as recited in claim 11, further comprising:
    tailoring prescribed functionalities performed by the vehicle based on said mapped driver ocular orientation.

13. The method as recited in claim 1, wherein said detected driver ocular orientation is exclusively derived based on a measure of gaze angularity.

14. The method as recited in claim 1, wherein said detected driver ocular orientation is derived at least partially based on a measure of gaze angularity.

15. The method as recited in claim 13, wherein said measure of gaze angularity is derived from a detected eyeball-orientation-based gaze-direction vector.

16. The method as recited in claim 7, wherein said detected head orientation is derived at least partially based on a measure of face-forward direction angularity.

17. The method as recited in claim 7, further comprising:
    establishing said definitions of probable locations of driver interest relative to said reference-base position based on detected head orientation from which a face-forward direction is deduced.

18. The method as recited in claim 17, further comprising:
    collecting a plurality of data points, each referencing a particular detected head orientation and hence a face-forward direction, and based upon said data points, establishing density mappings indicative of frequency at which a driver looks in a certain direction.

19. The method as recited in claim 18, further comprising:
    identifying a location of driver interest by correlating said mapping to probable locations of driver interest relative to said reference-base position.

20. The method as recited in claim 19, further comprising:
    tailoring prescribed functionalities performed by the vehicle based on said correlation.

21. The method as recited in claim 7, wherein said detected head orientation is exclusively derived based on a measure of face-forward direction angularity.

22. The method as recited in claim 21, wherein said measure of gaze angularity is derived from a detected head-orientation-based gaze-direction vector.

* * * * *